United States Patent [19]
Shikinami et al.

[11] Patent Number: 5,981,619
[45] Date of Patent: Nov. 9, 1999

[54] MATERIAL FOR OSTEOSYNTHESIS AND COMPOSITE IMPLANT MATERIAL, AND PRODUCTION PROCESSES THEREOF

[75] Inventors: Yasuo Shikinami; Masaki Okuno, both of Osaka, Japan

[73] Assignee: Takiron Co., Ltd., Osaka, Japan

[21] Appl. No.: 08/849,422

[22] PCT Filed: Sep. 13, 1996

[86] PCT No.: PCT/JP96/02642

§ 371 Date: May 14, 1997

§ 102(e) Date: May 14, 1997

[87] PCT Pub. No.: WO97/10010

PCT Pub. Date: Mar. 20, 1997

[30] Foreign Application Priority Data

| Sep. 14, 1995 | [JP] | Japan | 7-262353 |
| Dec. 25, 1995 | [JP] | Japan | 7-351503 |
| Dec. 25, 1995 | [JP] | Japan | 7-351504 |
| Jul. 31, 1996 | [JP] | Japan | 8-216874 |
| Jul. 31, 1996 | [JP] | Japan | 8-216875 |
| Jul. 31, 1996 | [JP] | Japan | 8-216876 |

[51] Int. Cl.$^6$ .......................... A61L 27/00; B29C 43/16; C08L 67/00
[52] U.S. Cl. .......................... 523/113; 523/114; 523/115; 524/414; 524/494; 525/450; 528/502 C; 264/320; 264/325; 264/328.1
[58] Field of Search .................. 264/328.1, 320, 264/325; 528/502 C; 523/113, 114, 115; 524/414, 494; 525/450

[56] References Cited

U.S. PATENT DOCUMENTS

| 4,968,317 | 11/1990 | Tormala et al. | 606/77 |
| 5,702,656 | 12/1997 | Sarver et al. | 264/320 |

FOREIGN PATENT DOCUMENTS

| 59-129124A | 7/1984 | Japan . |
| 61-248727A | 11/1986 | Japan . |
| 1-501289 | 5/1989 | Japan . |
| 1-198553 | 12/1989 | Japan . |
| 3-29663 | 2/1991 | Japan . |
| 5-3880 | 1/1993 | Japan . |
| 5-168647A | 7/1993 | Japan . |

*Primary Examiner*—Andrew E. C. Merriam
*Attorney, Agent, or Firm*—Sughrue, Mion, Zinn, MacPeak & Seas, PLLC

[57] ABSTRACT

A high bending strength and high density material for osteosynthesis, which comprises a biodegradable and bioabsorbable crystalline thermoplastic polymer material, and a high strength implant material, comprising a composite material in which a bioceramics powder of from 0.2 to 50 $\mu$m in particle size is dispersed in the polymer material, wherein crystals of the polymer material are pressure-oriented not in a uni-axial direction but basically in parallel with a plurality of reference axes; and a production method by pressure orientation, which comprises preparing in advance a biodegradable and bioabsorbable crystalline thermoplastic polymer material or a dispersed mixture of the polymer material and a bioceramics powder and melt-molding it into a pre-molded material which is then press-charged at a cold temperature into a cavity of a closed type forming mold, thereby obtaining an oriented molding. Since the osteosynthesis and implant materials are dense and high strength oriented moldings having less anisotropy in which crystals are oriented in parallel with a plurality of reference axes, excellent ideal biomaterials can be provided which have appropriate hydrolysis property, can maintain sufficient strength during a period required for bone union and are degraded and absorbed at such a rate that they do not induce inflammatory reactions after healing of the fractured bones so that re-operation is not required.

35 Claims, 12 Drawing Sheets

MATERIAL FOR OSTEOSYNTHESIS AND COMPOSITE IMPLANT MATERIAL, AND PRODUCTION PROCESSES THEREOF

TECHNICAL FIELD

This invention relates to most ideal biomaterials which can be substituted with the living body and are also useful in such applications as novel and effective artificial bones, artificial joints, artificial tooth roots, bone fillers, materials for osteosynthesis, bone prosthetic and the like that have bioactivities including the binding ability to the living body and inductivity of tissues, more particularly to a material for osteosynthesis having excellent physical strength, which comprises a crystalline thermoplastic polymer material that is degradable and absorbable in the living body, to an implant material comprising a composite material comprising the just described polymer material and bioceramics having bioactivities and to production processes thereof.

BACKGROUND ART

An implant could be regarded as one of ideal biomaterials, if it could be prepared from a material which is safe with no toxicity and can be present in the living body for a while by performing its mechanical and physiological functions and objects during the healing period, but is gradually degraded and disintegrated thereafter to be absorbed in the living body and excreted therefrom via the metabolic pathway in the living body, so that the region where it was implanted could finally be replaced by the living body to reconstruct original conditions of the living body.

In recent years, artificial bones, artificial joints, artificial tooth roots, bone fillers and bone prosthetic as substitutes for biological bones and cartilages which are hard tissues, and materials for osteosynthesis for the purpose of fixing fractured cartilages or hard bones in respective regions have been produced making use of various metals, ceramics and polymers.

In the field of surgery such as orthopedic surgery, plastic surgery, thoracic surgery, oral surgery, brain surgery and the like, plates, screws, pins and the like made of metals or ceramics are used as materials for osteosynthesis with the aim of fixing and binding biological bones.

However, being excessively high in mechanical strength and elastic modulus in comparison with biological bones, the materials for osteosynthesis made of metals have problems of, for example, causing a phenomenon of reduced strength of peripheral bones due to stress protection after the treatment. Also, the materials for osteosynthesis made of ceramics have excellent hardness and rigidity but are brittle, so that they have a fatal defect that it is apt to be broken. With regard to polymers, attempts are being made to improve their strengths which are generally lower than those of bones.

On the other hand, bioactive bioceramics which can be bound directly to bones have been used in many cases by directly implanting into or contacting with the human body, for the purpose of recovering or improving biological functions.

Also, certain bioceramics which bind directly and strongly to the living body and are gradually replaced by the living body have been studied continuously because of their unknown possibilities.

However, though their rigidity and hardness are generally large, the use of bioceramics as implants has a limitation because of their brittle properties of being easily chipped or broken by the momentary impact force in comparison with the case of metals, so that development of a material which has toughness but with no brittleness has been required in this field.

On the other hand, several cases have been known about polymers which are used as implants into peripheral areas of hard tissues, such as a silicone resin to be used as a substitute for cartilages, a hardenable acrylic resin as dental cement and braided cords made of polyester or polypropylene fibers for use in ligaments.

However, inert and high strength ultra-high molecular weight polyethylene, polypropylene, polytetrafluoroethylene and the other polymers to be used as substitutes for hard tissues in the living body are significantly lack in strength as substitutes for biological bones when used as such. Accordingly, when they are used alone in substitution bones or screws, pins or plates for osteosynthetic purpose, they are apt to be damaged by their breakage, splitting or wrenching.

In consequence, attempts have been made to produce implants having high strength, making use of compounding techniques of plastics.

A carbon fiber reinforced plastic material is an example of such case, but it is not practical, because peeling occurs between fibers and matrix plastic when implanted in the living body for a prolonged period of time, and the delaminated carbon fibers are broken and stimulate the living body to cause inflammation.

In recent years, a polyortho ester (a polybutylene terephthalate-polyethylene glycol copolymer) which is considered to be able to bind to bones has been drawing attention of this field. However, since the strength of this polymer itself is lower than the biological bones, it has a problem still remains unsolved, i.e. whether or not its physical behavior after its binding to bones in the living body can conform with the biological bones.

Unlike the case of the just described polymer which is not absorbable in the living body, polylactic acid, polyglycolic acid, lactic acid-glycolic acid copolymer and polydioxanone which are degradable and absorbable in the living body have been put into practical use for a long time in the clinical field as absorbable sutures.

It has been considered for a long time that if such polymers used in sutures could be applied to materials for osteosynthesis, it would be possible to obtain a material for osteosynthesis having such excellent properties that reoperation after healing is not necessary and reconstructing of biological tissues is effected after absorption and disappearance of the polymer.

In view of such an expectation, studies have been conducted actively on the use of the aforementioned biodegradable and bioabsorbable polymers as materials for osteosynthesis.

For example, a self-reinforced type devices for osteosynthesis in which polyglycolic acid fibers are fused has been proposed (U.S. Pat. No. 4,968,317, specification) and used in the clinical field, but its disadvantages have also been pointed out that it is degraded quickly and, though it is rare, the fused fibers are delaminated and fine pieces of the delaminated fibers stimulate their surrounding region in the living body to cause inflammation.

Also, an unexamined published Japanese patent application (Kokai) No. 59-97654 discloses a method for the synthesis of a polylactic acid and a lactic acid-glycolic acid copolymer which can be used as biodegradable and bioabsorbable devices for osteosynthesis, but it shows only the polymerization product itself as an example of the material for osteosynthesis, does not describe about molding process of the material and shows no attempts to improve its strength to a degree similar to that of the human bones.

In consequence, with the aim of improving such strength, proposals have been made on a method for the production of pins for osteosynthesis in which a biodegradable and bioabsorbable polymer material such as of polylactic acid or the like containing a small amount of hydroxylapatite (to be referred simply to as HA hereinafter) is molded and then drawn and oriented in the longitudinal axis direction with heating (an unexamined published Japanese patent application (Kokai) No. 63-68155) and on a material for osteosynthesis which is obtained by drawing a molded product of a high molecular weight polylactic acid or lactic acid-glycolic acid copolymer having a viscosity average molecular weight of 200,000 or more after its melt molding (an unexamined published Japanese patent application (Kokai) No. 1-198553).

In the materials and pins for osteosynthesis obtained by these methods, the crystal axis (molecular axis) of the polymer materials is basically uni-axially oriented in the longitudinal axis direction, so that their bending strength and tensile strength in the longitudinal axis direction are improved. Particularly, the latter case of material for osteosynthesis having a viscosity average molecular weight of 200,000 or more after its melt molding is practical, because it shows high strength even in its low drawing ratio that fibrillation does not occur.

However, in the case of materials for osteosynthesis obtained by drawing basically only in the longitudinal axis direction, molecules (crystals) are oriented basically only in the longitudinal axis direction which is the molecular chain axis (crystal axis), so that the orientation anisotropy along the transverse direction as the right angle direction to the longitudinal axis direction becomes large, and the strength in the transverse direction therefore becomes weak relatively.

Also, according to the aforementioned unexamined published Japanese patent application (Kokai) No. 63-68155, a maximum bending strength of 162 MPa is barely obtained by drawing a mixture containing 5% by weight of HA. However, when it contains 20% by weight of HA, the bending strength is rather reduced to 74 MPa which is slightly higher than the pre-drawing value of 63 MPa.

However, since this maximum strength value does not fully exceed those of cortical bones, and the material becomes a porous heterogeneous article in which voids generated by the drawing are present in a large number between fillers and matrix polymer, it cannot be used for implants which require high strength such as substitutes for biological bones and materials for osteosynthesis.

In addition, the above published patent application also describes about a method for the production of plates in which powder of a biodegradable and bioabsorbable polymer material such as polylactic acid containing a small amount of HA is press-molded, but the plates are produced merely by melt pressing of a mixture of HA and polylactic acid, and it does not describe a general idea of improving strength of the product taking its orientation into consideration.

In general, when biological bones are fixed using a material for osteosynthesis, forces in various directions are applied to the material for osteosynthesis. For example, in the case of a plate-shaped material for osteosynthesis, various forces such as bending force, tensile force, compressive force, tear force, shear force and the like are applied thereto, alone or in combination, and, in the case of a screw type material for osteosynthesis, a large torsional force is applied thereto when it is screwed into a biological bone and present in the living body, in addition to the above forces.

However, as described in the foregoing, in the case of a material for osteosynthesis obtained by drawing in the longitudinal axis direction, molecules are oriented only in the longitudinal axis direction which is the molecular chain axis [mechanical direction as the drawing axis], so that the molecular orientation anisotropy with the transverse direction as the right angle direction to the longitudinal axis direction becomes large.

Accordingly, the material is weak against tear strength from the longitudinal axis direction and shear breakage from the transverse direction and is also weak against torsional breakage which uses the longitudinal axis as the rotation axis. In consequence, when the just described tear force or shear force is applied to a material for osteosynthesis implanted in bones, the material for osteosynthesis will face a problem in that it is split or torn or generates shear fracture along a longitudinal axis direction relatively easily or a problem in that the material for osteosynthesis generates a torsional fracture when a torsional force is applied thereto using the longitudinal axis as the central axis of rotation like the case of a screw which is implanted in bones by loading a torque.

Such problems become more significant as the degree of fibrillation of the polymer material increases when its spherical structure reaches fibrous structure via a lamellar orientation by increased degree of drawing.

The present invention contemplates overcoming the aforementioned problems involved in the prior art, thereby providing biodegradable and bioabsorbable materials for osteosynthesis and implant which have less mechanical anisotropy and larger strength than a uni-axially oriented material obtained by longitudinal axial (uni-axial) drawing and in which their crystals are oriented basically not in the longitudinal axis direction but in parallel with a plurality of reference axes, as well as their production methods.

DISCLOSURE OF THE INVENTION

The present inventors have conducted extensive studies on the aforementioned problems and found that an oriented molding having larger strength than a uni-axially oriented material can be obtained easily by preparing in advance a pre-molded material comprising a biodegradable and bioabsorbable crystalline thermoplastic polymer material and then forcing it into a narrow space of a forming mold whose bottom part is basically closed, while carrying out plastic deformation at a cold temperature, thereby effecting pressure orientation, and that the aforementioned problems can be resolved by making an implant material from a novel composite material of which particles and matrix polymer are reinforced, which is a dense oriented molding in which a bioceramics powder whose particle or aggregated mass of particles has a size of from 0.2 to 50 μm is substantially uniformly dispersed in a biodegradable and bioabsorbable crystalline thermoplastic polymer (to be referred simply as "polymer" hereinafter) and the polymer crystals are oriented by pressure, thereby resulting in the accomplishment of the present invention.

Accordingly, the present invention provides:

(1) a material for osteosynthesis wherein (1) it is a material for osteosynthesis having high bending strength and high density which is a molding comprising a biodegradable and bioabsorbable crystalline thermoplastic polymer material in which its molecular chains or crystals are oriented not in a uni-axial direction but basically in parallel with a plurality of reference axes, (2) it is also characterized in that the polymer material described in (1) is a polylactic acid or a lactic acid-glycolic acid copolymer, (3) it is also characterized in that it is a pressure molding in which a part of the polylactic acid or lactic acid-glycolic acid copolymer is crystallized, (4) it is also characterized in that crystals of the aforementioned molding are oriented along reference axes slanted toward an axis which becomes mechanical core of said molding and/or continued faces of said axis, (5) it is also characterized in that the aforementioned molding is substantially in a columnar shape, and molecular chains or crystals are oriented along reference axes slanted from its peripheral side toward the central or off-central axis, (6) it is also characterized in that the aforementioned molding is substantially in a plate shape, and molecular chains or crystals are oriented along reference axes slanted toward the parallel face to both sides including axes located at the same distance or different distances from its both sides, (7) it is also characterized in that the aforementioned molding has a crystallinity of from 30 to 60%, (8) it is also characterized in that crystals of the aforementioned molding have crystal faces and face-oriented along reference axes, (9) it is also characterized in that the aforementioned molding is an oriented molding obtained by a compression molding or a forging molding in a closed type mold, and

(10) it is also characterized in that the aforementioned molding is a molding of a polylactic acid or a lactic acid-glycolic acid copolymer having a bending strength of from 160 to 300 MPa and a bending modulus of from 5 to 10 GPa,

[2] a method for producing a material for osteosynthesis wherein (1) it is a method for producing a material for osteosynthesis which comprises producing an oriented molding by preparing a pre-molded material through melt molding of a biodegradable and bioabsorbable crystalline thermoplastic polymer material and then forcing it into a narrow space of a forming mold whose bottom part is basically closed, while carrying out plastic deformation at a cold temperature and thereby effecting pressure orientation, (2) it is also characterized in that the oriented molding is crystallized and has a crystalline form in which said crystals are oriented basically in parallel with a plurality of reference axes, (3) it is also characterized in that the orientation by pressure deformation is effected by press-charging the pre-molded material described in (1) into a forming mold whose bottom part having a smaller sectional area than the sectional area of said molding is basically closed, while carrying out plastic deformation at a cold temperature and thereby effecting pressure orientation, (4) it is also characterized in that the orientation by pressure deformation is effected by forge-charging the pre-molded material described in (1) into a narrow space of a forming mold having a space which is smaller, partially or as a whole, than the sectional area, thickness or width of said molding, or into a forming mold having a space which is smaller than the volume of the pre-molded material, while carrying out plastic deformation at a cold temperature and thereby effecting the orientation, (5) it is also characterized in that initial viscosity average molecular weight of said polymer material is from 200,000 to 600,000, and viscosity average molecular weight of the pre-molded material melt-formed thereafter is from 100,000 to 400,000, (6) it is also characterized in that the pre-molded material is press-charged into the cavity of a forming mold having a cross sectional area which is from ⅔ to ⅙ of the cross sectional area of the pre-molded material, (7) it is also characterized in that the forming mold comprises a container cylinder part having large sectional area where the pre-molded material is contained, a cavity having small sectional area where the pre-molded material is press-charged and a diameter-reducing part having a taper face which connects the above parts, (8) it is also characterized in that plastic deformation temperature of the pre-molded material is a temperature effective in performing crystallization, which is between the glass transition temperature and the melt temperature of said thermoplastic polymer material, and (9) it is also characterized in that the oriented molding is made into a desired shape of the material for osteosynthesis by the means such as cutting work or the like,

[3] an implant material wherein (1) it is a high strength implant material which is a particle and matrix polymer reinforced composite material comprising a pressure-oriented molding in which from 10 to 60% by weight of a bioceramics powder whose particle or aggregated mass of particles has a size of from 0.2 to 50 μm is dispersed substantially uniformly in matrix of a biodegradable and bioabsorbable crystalline thermoplastic polymer, wherein crystals of said matrix polymer are oriented by pressure and have a crystallinity of from 10 to 70%, (2) it is also characterized in that crystals of the aforementioned molding are basically oriented in parallel with a plurality of reference axes, (3) it is also characterized in that the bioceramics powder is any one or a mixture of two or more of surface bioactive sintered hydroxylapatite, bioglass or crystallized glass for living body use, bioabsorbable un-sintered hydroxylapatite, dicalcium phosphate, tricalcium phosphate, tetracalcium phosphate and octacalcium phosphate, (4) it is also characterized in that the biodegradable and bioabsorbable crystalline thermoplastic polymer is either a polylactic acid or a lactic acid-glycolic acid copolymer, and its initial viscosity average molecular weight is from 100,000 to 600,000, (5) it is also characterized in that the thermoplastic polymer is a polylactic acid and the bioceramics powder is an un-sintered hydroxylapatite, (6) it is also characterized in that the aforementioned molding is an oriented molding obtained by pressure orientation through a compression molding or a forging molding, (7) it is also characterized in that the aforementioned molding has a bending strength of from 150 to 320 MPa and a bending modulus of from 6 to 15 GPa, and (8) it is also characterized in that the aforementioned oriented molding is treated by the means such as cutting work or the like, and the bioceramics powder is exposed on the surface thereof, and

[4] a process for producing an implant material wherein (1) it is a method for producing a high strength implant material by pressure deformation orientation which comprises preparing in advance a mixture in which a biodegradable and bioabsorbable crystalline thermoplastic polymer and a bioceramics powder are dispersed in each other substantially uniformly, subsequently producing a pre-molded material (a billet for example) by melt molding of said mixture and then press-charging said pre-molded material at a cold temperature into the cavity of a closed type forming mold, thereby effecting plastic deformation and formation of an oriented molding, (2) it is also characterized in that the aforementioned pressure orientation is effected by press charging at a cold temperature into the cavity of a closed type forming mold having a smaller sectional area than that of the pre-molding, (3) it is also characterized in that the pre-molded material is press-charged into the cavity of a closed type forming mold in such a manner that crystallinity of the polymer of the molding obtained by pressure orientation becomes from 10 to 70%, (4) it is also characterized in that the mixture of the aforementioned polymer and bioceramics powder is prepared by substantially uniformly mixing and dispersing the bioceramics powder in a solvent solution of the aforementioned polymer and subsequently precipitating the mixture with a non-solvent of said polymer, (5) it is also characterized in that the biodegradable and bioabsorbable crystalline thermoplastic polymer is a polylactic acid or a lactic acid-glycolic acid copolymer having an initial viscosity average molecular weight of from 150,000 to 700,000, and a viscosity average molecular weight of from 100,000 to 600,000 after its melt molding, (6) it is also characterized in that the pre-molded material is press-charged into the cavity of a forming mold having a cross sectional area which is from $2/3$ to $1/5$ of the cross sectional area of said pre-molded material, (7) it is also characterized in that plastic deformation temperature of the pre-molded material is a temperature effective in performing crystallization, which is between the glass transition temperature and the melt temperature of said polymer, (8) it is also characterized in that the orientation by pressure deformation is effected by compression orientation or forging orientation, and (9) it is also characterized in that the aforementioned pressure oriented molding is further processed by the means such as cutting work or the like.

The following describes the present invention in detail.

(A) Material for Osteosynthesis of the Present Invention (a) Crystal Structure (1) The material for osteosynthesis of the present invention is basically 1) a molding which comprises a biodegradable and bioabsorbable crystalline thermoplastic polymer material (to be referred simply as "polymer material" hereinafter) and 2) characterized in that molecular chains or crystals which constitute the molding are oriented not along a single axis but basically in parallel with a plurality of reference axes.

In this case, anisotropy in view of strength of the molding becomes small as the number of reference axes becomes large, so that its breakage hardly occurs.

This is described illustratively with reference to the drawings.

(2) FIGS. 1 to 3 are schematic illustrations showing orientation conditions of oriented moldings obtained by a pressure deformation through forcing into a closed type mold, for example, by deformation through compression molding or forging molding (to be referred simply to as "compression molding, compression orientation" or "forging molding, forging orientation" hereinafter).

FIG. 1 is a schematic illustration showing orientation conditions of a cylinder shaped material for osteosynthesis 11, and FIG. 1(A) shows orientation conditions of its longitudinal section, and FIG. 1(B) shows orientation conditions of its plane.

FIG. 2 is a schematic illustration showing orientation conditions of a plate shaped material for osteosynthesis 11 and FIG. 2(A) shows orientation conditions of its longitudinal section, and FIG. 2(B) shows orientation conditions of its plane.

FIG. 3 schematically illustrates orientation conditions of crystals on a longitudinal section of the molding, and FIG. 3(A) shows orientation conditions when an axis or face which becomes mechanical core is located at the central position or a position having the same distance from both sides, FIG. 3(B) shows the conditions when the aforementioned axis or face is displaced from the central position or a position having the same distance from both sides, FIG. 3(C) shows the conditions when the aforementioned axis or face is completely displaced and FIG. 3(D) shows orientation conditions of a conventional uni-axially oriented molding obtained by its drawing in the longitudinal axis direction.

FIG. 4 is a sectional view showing an example of the production of the material for osteosynthesis 11 by compression molding.

(3) For example, when the compression molding shown in FIG. 4 is used, a pre-molded material (to be referred to as "billet" hereinafter; production method of this pre-molded material will be described later in detail) 1 obtained by melt molding of the polymer material is put into a container cavity 2a which has a large diameter and is arranged on the upper part of a forming mold 2 whose bottom end is closed and then subjected to compression molding by forcing it into a bottomed forming cavity 2c which has a concentric circle shape having throttled and reduced diameter on its way down, using a male mold (piston) 2b or a ram or the other means at a cold temperature (a temperature at which crystallization can be effected but is lower than the conventional molding temperature which is equal to or higher than the melt temperature, namely a temperature between the glass transition point and melt temperature of the polymer material as will be described later, for example, from 60 to 160° C. in the case of a polylactic acid or a lactic acid-glycolic acid copolymer), thereby resulting in a crystalline form of the molding in which, as shown in FIG. 1, crystals are not uni-axially oriented but basically oriented in parallel with a plurality of reference axes N lined from the circumference toward the central position.

(4) As schematically shown in FIG. 1, crystals which constitute the oriented molding are oriented continuously and in parallel from the upper part toward the lower part of FIG. 1(A) along a large number of reference axes N which are slanted from the peripheral side toward an axis L which becomes mechanical core of the molding (to be referred simply to as "central axis" hereinafter), namely a central axis L of continued mechanical points to which outside forces are concentrated at the time of molding.

In other words, a large number of reference axes N in a radially slanted orientation state around the central axis L form a roughly conical shape by connecting toward the peripheral direction as shown in FIG. 1(B) and are connected in vertical direction as shown in FIG. 1(A), so that the crystals constitute continuous phase of roughly conical faces by orienting in parallel with these reference axes N. That is, it can be regarded as an orientation structure in which said conical crystal faces continue in the vertical direction along the central axis L, and the crystal faces directing from the peripheral side toward the central position are oriented along the central axis direction.

Such a crystalline condition is effected by receiving large shear force when the billet 1 is compression-molded and simultaneously generating diagonal orientation toward the central axis L as the crystallization progresses.

In this case, when a large billet 1 having a rectangular section is compression-molded in a forming cavity 2c having a rectangular section, as shown in FIG. 2, the thus obtained oriented molding has a plate shape, and the axis which becomes mechanical core by receiving large shear force from both longitudinal sides does not become the central line, but a face M is formed which contains this axis and is located in parallel with and at the same distance (the middle) from the facing sides of the plate. In consequence, crystals of the oriented molding are oriented in parallel with the diagonal reference axes N directing from both facing sides of the plate toward said face.

In addition, since the axis L or the face M which contains said axis L, that becomes mechanical core of the molding, is a point where forces from the outside are concentrated, when a bottomed forming mold 2 such as the forming mold 2 shown in FIG. 4 in which inclination angle of the diameter-reduced taper face side 20a is gradually changed partially or over the entire peripheral is used, the point where the outside forces are concentrated is displaced from the center, and the crystals are oriented in parallel with the reference axes N which are changed in response to the inclination angle slanted from the peripheral side toward the displaced axis L (this could be present in plural numbers). Also, when the oriented molding has a plate shape as shown in FIG. 2, the face M of continued axis L to be served as the mechanical core is not located at the same distance (the middle) from both sides but inclined toward either one of the sides.

Typical examples of such orientation conditions of crystals are described with reference to the longitudinal sections of the molding of FIG. 3.

FIG. 3(A) shows orientation conditions when the aforementioned axis L or face M passes through the center or middle of the molding, in which the crystals are oriented in parallel with the reference axes N slanted from both sides toward the axis L or face M at the same angle.

FIG. 3(B) shows orientation conditions when the aforementioned axis L or face M is displaced toward the right side, in which the crystals are oriented in parallel with the reference axes N and N' slanted from both sides toward the displaced axis L or face M at different angles.

FIG. 3(C) shows orientation conditions when the aforementioned axis L or face M is completely inclined toward the left side, in which the aforementioned axis L or face M is located at the left side end, and the crystals are oriented in parallel with the reference axes N slanted from the right side toward the axis L or face M located at the left side end.

FIG. 3(D) shows conditions of crystals of a usual uniaxially drawn molding, in which the crystals are oriented in vertical direction as a lengthwise reference axis N which is the drawing direction, and the reference axis N is not present in plural numbers.

(b) Crystallinity

According to the material for osteosynthesis of the present invention, its molding should have a crystallinity of from 30 to 60%, preferably from 40 to 50%.

When the molding has a crystallinity within such a specified range, crystal phase and amorphous phase of the crystalline thermoplastic polymer which constitutes the molding have a well balanced ratio, and improvement of the strength and hardness effected by the crystalline phase is suitably matched with the flexibility effected by the amorphous phase, so that the molding shows no brittleness which is common in the case of only crystal phase, and weak property with no strength which is common in the case of only amorphous phase is not generated.

In consequence, the material for osteosynthesis of the present invention has toughness, its total strength becomes sufficiently high and particularly its torsional strength becomes high, so that it becomes useful as a material for osteosynthesis.

In the case of such a crystalline thermoplastic polymer which is degradable and absorbable in the living body, it is known in general that its crystallinity gradually increases during a period in which it is changed into small molecules with the progress of its hydrolysis in the living body. Since the progress of its hydrolysis becomes slow as the crystallinity increases, the polymer is not easily hydrolyzed into sufficiently small molecules to be absorbed by the living body.

However, decrease in the hydrolytic rate seldom occur in the living body when the polymer has the aforementioned range of the specified initial crystallinity.

According to the material for osteosynthesis of the present invention, improvement of strength by crystals cannot generally be expected when crystallinity of the molding is less than 30%. On the other hand, though the strength increases as the crystallinity increases, its level exceeding 60% will cause significant generation of a brittle property and the molding is easily broken when it receives a force such as an impact or the like due to lack in toughness and also will delay the hydrolytic rate in the living body due to obstructed penetration of water into crystals. Also, a large number of fine crystal pieces generated during a certain period will cause stimulation of peripheral tissues in the living body.

In consequence, it is desirable to control the crystallinity to from 30 to 60%, by taking a balance between these two objects, namely the antinomic nature between physical properties as strength and toughness and degradation behavior of the biodegradable and bioabsorbable polymer in the living body.

In this connection, when the material for osteosynthesis has a relatively large shape, it requires a larger strength than a certain level and a prolonged period of time until its degradation and absorption, so that its preferred range of crystallinity in that case is from 40 to 50%.

(c) Oriented Molding Obtained by a Pressure Deformation Orientation (for Example, Compression Orientation or Forging Orientation)

The material for osteosynthesis of the present invention is a qualitatively dense oriented molding obtained by a pressure deformation orientation.

In this case, since the molding becomes qualitatively dense by its pressurization in the pressurization direction, in addition to the reduction of anisotropy of the crystal form by the crystal orientation, its mechanical properties such as bending strength, bending modulus, tensile strength, tear strength, torsional strength, surface hardness and the like are sharply improved.

(d) Composition of Biodegradable and Bioabsorbable Polymer Material

The polymer material to be used in the present invention is not particularly limited, with the proviso that it is a crystalline straight chain polymer which is degradable and absorbable in the living body, and its preferred examples include a polylactic acid and various polylactic acid copolymers (for example, a lactic acid-glycolic acid copolymer, a lactic acid-caprolactone copolymer and the like) which have been already put into practical use after confirmation on their biological safety and biocompatibility.

Homopolymer of L-lactic acid or D-lactic acid is desirable as the polylactic acid, and, as the lactic acid-glycolic acid copolymer, a copolymer having a molar ratio within the range of from 99:1 to 75:25 is desirable because of its superior hydrolysis resistance to that of glycolic acid homopolymer.

In addition, amorphous D,L-polylactic acid or an amorphous lactic acid-glycolic acid copolymer having a relatively high ratio of glycolic acid may be mixed in a small amount in order to facilitate plastic deformation or to let the oriented molding obtained by compression orientation have toughness.

(e) Molecular Weights of Polymer Material and Pre-molded Material

The aforementioned polymer material requires certain physical properties, at least strength of a certain degree or more and the ability to keep it during a certain period of time, as the material for osteosynthesis, but molecular weight of said polymer material decreases at the stage of its melt molding into a pre-molded material such as a billet or the like, so that it is desirable that the material polymer has a viscosity average molecular weight of approximately from 200,000 to 600,000, preferably from 300,000 to 550,000.

When a polymer material having a viscosity average molecular weight within this range is used, viscosity average molecular weight of the billet after melt molding generally becomes from 100,000 to 400,000, but it is desirable to adjust it to from 180,000 to 350,000.

Since the subsequent orientation process of crystals by press charging into a forming mold is carried out at a cold temperature within the aforementioned range for a short period of time, a compression orientation molding having high strength can be obtained without substantially reducing its molecular weight, and a material for osteosynthesis in which the molecular weight of compression orientation molding is maintained can be obtained when some means are applied to prevent increase in temperature caused by friction at the cutting step of the material for osteosynthesis by the means such as cutting work or the like.

In this case, when a polymer material having an initial viscosity average molecular weight of higher than 600,000 is used, a high temperature and a high pressure are required when a billet is produced by melt molding, so that it causes sharp reduction of its molecular weight to a meaningless level which is even lower than a case in which a material polymer for billet having a molecular weight of less than 600,000 is used.

A screw 30 for osteosynthesis shown in FIG. 6, which is produced by a cutting work of the compression orientation molding obtained from a billet having a final molecular weight of approximately from 100,000 to 400,000, is desirable, because it maintains similar strength to that of the biological bone for from 2 to 4 months, a period required for bone union in the living body, and is then gradually hydrolyzed at such a degradation rate that small pieces generated by degradation of the material for osteosynthesis do not exert strong foreign body actions upon peripheral tissues and cells and therefore do not cause inflammatory reactions.

When viscosity average molecular weight of the billet after melt molding becomes lower than 100,000, the oriented molding obtained by compression molding can hardly have high initial strength, and reduction period of the strength by hydrolysis is shortened to less than 2 months, thus posing a problem of not maintaining the strength during a period necessary for bone union.

Also, since low molecular weight small pieces may sometimes be generated at one time within a short period of from 1.5 to 2 years after its implantation into the living body, there is a possibility in that the peripheral cells cannot treat these pieces, thus posing a danger of inducing inflammation by foreign body reaction.

On the other hand, a material for osteosynthesis produced as an oriented molding by compression molding using a billet having a viscosity average molecular weight of higher than 400,000 after its melt molding requires unnecessarily long period until it is degraded and completely absorbed after bone union in the living body. In addition, there is a danger in that a large number of low molecular weight small pieces generated at one time after a long period of 2 years or more of its implantation into the living body would cause foreign body reaction and induce inflammation in the living body.

(f) Physical Properties etc. of Material for Osteosynthesis (1) Density

The material for osteosynthesis of the present invention is in any case a compression-oriented molding obtained by adding three-dimensional forces to the material in the inner direction. Accordingly, when it is compared with the conventional drawn and oriented molding obtained by adding forces in the departing direction from the material, the material for osteosynthesis of the present invention is characterized in that it has a density of from 1.25 to 1.27 $g/cm^3$ which is higher than 1.25 $g/cm^3$ or less of the latter drawn and oriented molding. The case in which the aforementioned density is low, namely 1.25 $g/cm^3$ or less, is not preferable, because denseness of the material is relatively low, orientation condition of the crystals becomes close to the orientation condition by uni-axial drawing and the anisotropy becomes large. Also, when the value is large exceeding 1.27 $g/cm^2$, the crystallinity inevitably becomes 70% or more, so that such a case is not desirable because of the aforementioned reasons.

(2) Physical Properties and the Like

Though mechanical strength of the material for osteosynthesis of the present invention basically shows a tendency to increase as initial viscosity average molecular weight of the polymer material increases, the polymer becomes hardly fluidal at the time of heating when its initial viscosity average molecular weight is too large exceeding 600,000, so that a high temperature and a high pressure are required when a billet is produced by melt molding. Accordingly, its molecular weight is rather sharply reduced due to exothermic reaction caused by shear force at the time of molding, so that molecular weight of the finally obtained material for osteosynthesis may become smaller than the aforementioned value and its strength may also become small, thus resulting in a meaningless product.

The material for osteosynthesis of the present invention shows generally high mechanical strength values of from 160 to 300 MPa as bending strength, from 5 to 10 GPa as bending modulus and from 5.5 to 7.5 kg·cm as torsional strength with a rod of 3.2 mmφ.

According to the present invention, full functions as the material for osteosynthesis cannot be obtained when its bending strength is less than 160 MPa which is smaller than that of human bone, and a material having a large strength of exceeding 300 MPa can hardly be obtained even under a pressure. The bending modulus and torsional strength of the present invention are within sufficient ranges to be used as a material for osteosynthesis.

(B) Implant Material of the Present Invention

Firstly, from the viewpoint of composite material, it is revealed that the present invention is a composite material of a novel reinforcing system.

(a) Characteristics of the Composite Material of the Present Invention (1) When characteristics of a material is improved by dispersing a large amount of a fine material therein, the former is called a mother material (matrix), and the latter a dispersed material. A composite material is produced by not a microscopic mixing of these two materials at a molecular level but by their macroscopic mixing in such a manner that the product can get an excellent property which cannot be found in each material.

The method for producing a material having more excellent properties (higher strengths) by compounding these different materials can be classified as follows depending on the form of dispersed materials (reinforcing materials) to be dispersed in the matrix.

(i) Dispersion-strengthened composite materials,
(ii) particle-reinforced composite materials, and
(iii) fiber-reinforced composite materials.

The implant material of the present invention belongs to the composite material of (ii). The polymer as the matrix is a polylactic acid or a copolymer thereof which is a thermoplastic and crystalline polymer that is degradable and absorbable in the living body, and the dispersed material is the aforementioned bioceramics in the form of fine particle powder.

(2) By the way, implants as composite materials produced by the combination of (iii) was considered to be of promise from the viewpoint of material technology, and there was a time in which a large number of studies were conducted on such materials in this field. However, good results have not been obtained for example by a reinforcing method in which short fibers of bioceramics are charged as the dispersed material, because the fiber pieces caused inflammation by stimulating the living body.

Also, the self-reinforced type method described in the foregoing, having the same type of the fiber-reinforced method in which fibers of a polylactic acid or a polyglycolic acid are fused on the surface, has also been studied. However, a disadvantage was found in that fusion surfaces among fibrils are microscopically heterogenous so that fibers are easily separated and the degraded small pieces stimulate the living body in some cases.

Since biomaterials must exert no toxicity upon the living body, be safe and have biological affinity, such a method is disqualified in view of these points.

(3) Even in the case of the filler-charged type composite materials of (ii), a composite material having the high strength of the present invention cannot easily be obtained by simply mixing a bioceramics powder with a matrix polymer in accordance with the conventional method.

In general, properties of a filler-charged composite material basically depend on the forms [shapes (powder, sphere, plate and the like) and size and surface area of particles] and functions (in this case, binding ability to the hard tissue such as bones, bone inductivity, bone conductivity and the like inducing abilities and bioabsorbability) of fillers and properties of the polymer. Mechanical characteristics are greatly influenced by the factors such as content, form, orientation, surface force and the like of the matrix polymer and fillers.

Since these various factors are mutually related to one another under complex conditions, it is necessary to thoroughly understand influences of each factor upon total characteristics, in order to generate intended structural characteristics and functional characteristics.

(4) This point is described in further detail.

In the case of a composite material charged with a filler, characteristics by which significant effects are generated include elastic modulus, tensile strength, elongation characteristics, toughness, hardness and the like. In the case of the filler-charged type composite material of the present invention, bioceramics particles having extremely small L/D (length/diameter) are selected, so that elastic modulus of the composite material, which reflects high rigidity of the bioceramics, can be increased effectively to a higher level than the elastic modulus of the matrix polymer itself, by increasing charging amount of the filler.

However, the properties such as tensile strength, elongation, toughness and the like are apt to decrease as the charging amount increases. In consequence, it becomes a subject to find how to increase elastic modulus, while simultaneously increasing other characteristics to higher strengths than those of the original matrix polymer.

In other words, it can be said that the compounding is a technique how to bring out excellent characteristics of the dispersed-material and matrix in a synergistic fashion, while compensating disadvantages. While elastic modulus is a value of a region of small deformation degree, mechanical characteristics such as tensile strength, bending strength, torsional strength, elongation, toughness and the like are revealed in a region of relatively large deformation degree.

In consequence, influence of surface adhesive strength between particles and matrix upon elastic modulus is small, but its influence is exerted greatly upon the latter various physical properties. Thus, one can realize that excellent results of the latter physical properties can be obtained when the surface adhesive strength is increased.

(5) A positive method for increasing surface adhesive strength is to combine a polymer as the matrix with bioceramics as the dispersed material using a coupling agent. Several coupling agents, typically those of silicone system and titanium system, are used in composite materials aimed at their industrial use. Thus, these agents may be used.

However, it cannot be said at present that safety of this type of compounds upon the living body has been deeply examined. Though these coupling agents are used in dental bone cement which is a non-absorbable high filling material, we know of no report concerning their practical application to medical materials which are degradable and absorbable in the living body, so that their application to the present invention should be avoided for the time being while their safety is unknown.

That is, the method in which the surface strength is increased by chemically combining a matrix polymer and bioceramics fine particles should not be applied to implants for hard tissue use which are degraded and absorbed in the living body and replaced by tissues like the case of the present invention, because, different from the non-absorbable implants, these coupling agents whose safety is not yet confirmed are gradually exposed during the degradation process. Also, they are not desirable because they spoil the surface activity of bioceramics.

(6) By the way, it is known that impact strength, tensile strength and elongation at rupture relatively increase in general when the degree of dispersion of fine particles is improved in a system in which a thermoplastic crystalline polymer is mixed with the same concentration of fine particles.

In the same manner, the size of fine particles exert great influences upon physical properties of composite materials, and impact strength, tensile strength, compressive strength, elastic modulus and the like generally increase relatively when the particle size becomes small at the same concentration.

The reason for this is that, since the surface area increases relative to the reduced particle size, surface energy increases relatively, contacting area to the polymer also increases and the small particles effectively function as nucleating agent for crystallization of the polymer, so that physical bonding between the dispersed material and the matrix is reinforced as the result.

When the above facts are taken into consideration, it is best to mix ceramics fine powder as small as possible under dispersion conditions as good as possible within a certain range of concentration.

(7) However, these problems cannot easily be resolved by the aforementioned simple mixing when it is necessary to obtain a composite material such as the case of the present invention in which extremely high strength similar to or higher than the cortical bones is added thereto and a complex function to effect early stage healing and substitution of biological bones through induction and conduction of bones is also added thereto by mixing bioceramics with a thermoplastic crystalline polymer which is degradable and absorbable in the living body.

(8) The following describes illustrative means for resolving problems of the present invention.

When particle size of inorganic fine powder becomes small, surface area of the particles becomes large accordingly, so that the particles easily receive secondary aggregation even by the generation of a small electric charge on the surface, thereby always forming an aggregated mass having much larger diameter than that of a single particle.

Accordingly, it is not technically easy to obtain a uniform dispersion system which does not contain large aggregated mass of fine particle, in a particle-reinforced composite material having relatively high filler concentration. Easiness to form a secondary aggregated mass varies depending on the chemical structure of fine particles, and the bioceramics fine particles to be used in the present invention form an aggregated mass relatively easily under well dried conditions. It is common that particles of several $\mu$m in average particle size aggregate to form a mass having a diameter of 100 $\mu$m or more.

(9) In this connection, it is known that strength such as notch Charpy impact or the like which does not accompany large deformation is independent of the size of aggregated mass but depends on the maximum size of each particle.

Also, when the forces such as bending, tensile, torsional and the like which cause large deformation and final breakage are added to a composite material, it is always broken at the time of deformation which is smaller than the deformation that breaks the matrix polymer itself.

These phenomena occur when relatively large particles or aggregated masses which are presented in the matrix but different from the polymer show different physical behavior from that of the matrix accompanied by deformation.

That is, since the surface between the matrix and particles is a discontinued part in which the outside deformation energy propagated through the matrix cannot be transferred as such, breakage occurs at this surface.

(10) However, when particles are dispersed finely and uniformly, different from the case in which large particles and aggregated masses are present, such a barrier for the propagation of energy is small and the deformation energy therefore receives less resistance and are propagated throughout the system, so that the matrix polymer of the composite material is broken at a deformation quantity which is more close to the point of deformation breakage of the polymer alone.

In other words, it can be said in general that, when a filler-charged composite material under a poor dispersion condition, for example in which large particles are present (even when they are uniformly dispersed) or small particles form a large aggregated mass, is broken by receiving large deformation, the strength rather becomes smaller than the strength at the time of the breakage of the matrix polymer itself containing no dispersed particles.

(11) Accordingly, when high mechanical strength is required, it is absolutely necessary to prepare a uniform dispersion system which is composed solely of particles having such a small particle size that they hardly exert influences upon the deformation quantity and strength at the time of deformation breakage and in which large aggregated masses are not formed.

That is, according to the bioceramics fine particles of the present invention, it is necessary to select them from those which have a particle size of approximately from 0.2 to 50 $\mu$m, more preferably from 1 to a little over 10 $\mu$m, which are obtained by sintering the material at an appropriate temperature [for example, from 600 to 1,250° C. for hydroxylapatite (HA), 1,500° C. for apatite wollastonite glass ceramics (AW) or from 1,150 to 1.400° C. for tricalcium phosphate (TCP)] and then mechanically pulverizing and screening the sintered product, and to use a uniformly dispersed system thereof in which their aggregated mass also has a diameter of from 50 $\mu$m or less.

As a matter of course, sintering and pulverization are not necessary in the case of un-sintered HA (V-HA) synthesized by a wet method, and crystal particles precipitated at the time of synthesis having the above range of size can be used as such. Not only such a range of particle size is necessary to satisfy the aforementioned physical strength, but it also has an important relation with the reactivity shown by peripheral osteoblasts as will be described later. In a system which satisfies these conditions, the strengths such as impact strength, surface hardness, elastic modulus and the like at the time of receiving a small deformation are improved, and the strengths such as bending, tensile, torsional and the like of the matrix polymer itself at the time of receiving a large deformation are also expressed, so that it is a composite material having further increased rigidity.

(12) An effective means for mixing bioceramics which aggregate relatively easily such as the case of HA without causing secondary aggregation in the matrix is to thoroughly disperse the bioceramics in a polymer dissolved in a solvent and precipitate the dispersed system with a non-solvent.

They can be mixed with a bioceramics/polymer weight ratio of from a low ratio of 10% or less to a high ratio of exceeding 60%.

When the amount of bioceramics to be added is less than 10%, volumetric ratio of the bioceramics is small, so that properties to be expected by the bioceramics, such as direct bonding to bones, bone conduction and bone induction, are not easily revealed, and substitution by the biological bones is also slow.

Also, when the amount exceeds 60%, molding cannot easily be effected because of insufficient fluidity of the mixture system at the time of thermoforming. Also, since proper binder effect is not obtained due to insufficient amount of the polymer in the formed product, the filler and polymer are apt to be separated and the product becomes brittle from the viewpoint of strength. Particularly, a case in which the amount of filler is large exceeding 70% and the polymer is smaller than 30% is not desirable, because the effect of the polymer to bind bioceramics powder is reduced when the composite material becomes brittle by degradation of the polymer, and the powder scatters to induce tissues reactions of the peripheral tissues.

When the above problems are taken into consideration, the mixing ratio is preferably from 20 to 50% by weight, most preferably from 30 to 40% by weight. Within this range, desirable characteristics of both the dispersed material and matrix are markedly revealed as the composite material from both structural and functional points of view.

Thus, conditions, objects and methods for obtaining a uniform dispersion have been described in the foregoing from the viewpoint of obtaining a mixture system of bioceramics and a polymer.

(13) However, a biomaterial which exceeds the strength of high strength plastics and also exceeds the strength of cortical bones (from 150 to 200 MPa in bending strength) cannot be obtained even when the composite material in which the polymer and filler are uniformly dispersed in the above manner is processed by the usual thermoforming.

In general, it is difficult to carry out thermoforming of a polymer containing a large amount of filler because of poor fluidity. It is much more difficult to carry out thermoforming when a titanium coupling agent which is markedly effective in improving fluidity cannot be used because of the necessity to consider safety on the living body such as the case of the present invention.

When such a composite material of a polymer and ceramics powder, having poor fluidity, is thermo-formed by extrusion molding, a molding method in which shear force is added at the time of kneading and melting, the polymer itself performs deformation flow with its original flow characteristics, but the charged inorganic filler does not have a property to flow by plasticizing with heat, so that cavities (voids) are formed due to cleavage on the surface of the polymer and filler particles at the time of flow deformation transfer, thereby entailing a formed product of rough density.

A porous molding containing a large number of voids is low in strength. In consequence, in order to prevent formation of voids, compression type molding methods such as injection molding, press molding and the like are used for the molding of such a type of polymer charged with a large amount of filler.

(14) However, a molding having high strength cannot be obtained by such conventional molding methods, because the polylactic acid or copolymer thereof of the present invention is easily heat-deteriorated by shear force or deteriorated by considerable hydrolysis caused by a small amount of water contained therein.

Though a heterogeneous plate or the like having somewhat less deterioration of the polymer but having flow marks might be formed when heating condition, drying condition and molding condition of the press molding are strictly controlled, a strength which exceeds that of cortical bones cannot still be obtained because the polymer itself is not reinforced at the level of its molecular structure or higher-order structure.

(15) Drawing can be used as a method to increase strength of crystalline thermoplastic polymers such as poly L-lactic acid and copolymers thereof. This is a deformation processing in which a primary molding such as a rod or the like is uni-axially drawn in the longitudinal axis direction by drawing both ends, or one end while fixing the other end, of the molding in the outward direction from the molding at a specified temperature (equal to or lower than Tm, a temperature at which the polymer melts and flows), thereby effecting orientation of molecular chains or the thus formed crystal phase in the drawing direction (MD) and obtaining a secondary molding having further increased strength.

Though its object and method are different from those of the present invention, the aforementioned examined Japanese patent publication (Kokoku) No. 3-63901 disclosed a method in which HA is mixed in a small amount of from 1 to 15% and the resulting primary molding is uni-axially drawn in the longitudinal axis direction.

However, as described in the foregoing, the polymer itself moves in the mechanical direction accompanied by plastic deformation of the polymer, but the filler particles themselves do not move by completely synchronizing with the plastic deformation, so that generation of voids during the drawing due to formation of cleavage on the surface between the particles and polymer cannot be avoided. Particularly, a movement in which material per unit volume becomes more thin occurs by a force of drawing in the case of the above free width uni-axial drawing by the longitudinal axis direction drawing which is a method in which external force is not added from a direction vertical to the drawing direction during the drawing step.

As a consequence, the polymer changes from its microfibril state into fibrillated condition when the draw ratio is increased, but density of the material is further reduced because of the formation of microscopic discontinued spaces between fibrils under such a condition.

(16) This fact suggests that, in a molding obtained by drawing a composite material in which a filler is dispersed in a large amount, the number of voids becomes large as the charged amount of filler becomes large, and the size of voids becomes large as the deformation quantity becomes large (as the draw ratio becomes large).

In a system in which the size of filer particles is not controlled, their dispersion is poor and large aggregated masses are present, the number of voids and their size are much more heterogeneous.

In fact, since such a type of composite material which contains voids is easily broken during its drawing, a drawn material of object cannot be obtained.

In consequence, a molding having high strength required by the present invention cannot at all be obtained from a drawn composite material which contains voids.

(17) In view of the above, the inventors of the present invention have conducted extensive studies and achieved the object by the following molding method. In this method, as described in the foregoing, a billet of said polymer containing a large amount of uniformly dispersed bioceramics is melt-molded under such conditions that heat deterioration is controlled at a level as low as possible (for example, by extrusion or compression molding), and the thus treated billet is then made into an oriented molding by compression molding or forging molding for the purpose of effecting compression orientation of the polymer.

According to this method, external force at the time of orientation molding is applied in the inward direction, namely toward the material itself contrary to the drawing direction, so that the material becomes a dense condition.

Accordingly, the surface between particles and matrix is changed into a more close state, and even the microscopic voids formed in the mixing step via air presented in the surface disappear, so that a high denseness is obtained. In other words, both materials become more integrally bonded structure.

In addition to the above, since the molecular chain axis and crystal phase are oriented in the matrix polymer, the resulting composite material shows markedly high strength.

In this case, it seems that the orientation of crystals effected by deformation obtained by press-charging a billet as a primary molding into the cavity of a mold having a sectional area smaller than the sectional area of said billet partially or over the entire region takes a form having a strong tendency to perform surface orientation in parallel with certain reference axes, unlike the case of uni-axial orientation formed by simple drawing in the longitudinal axis direction, because a force is added by a "shearing" from the mold (forming mold).

Accordingly, the characteristics of small anisotropy by orientation and strong resistance against torsion or the like deformation are revealed. The degree of orientation is controlled at such a basic level that the molecular chain lamella can orient and not at a high level at which voids are generated by microfibrils and fibril structure which can be found when the draw ratio is high.

(18) Thus, reinforcing method of the composite material of the present invention has been described, and its mode is evidently different from those of the conventional composite materials as shown in FIG. 15.

That is, the conventional particle-reinforced type (a) and fiber-reinforced type (b) are methods which aim at generating physical strength of the respectively charged particles 13 and fibers 14 in each system by increasing their charging ratios as high as possible and also at increasing the strength basically depending on their chemical and physical powers to bind to the matrix polymer.

In the fiber-reinforced type (b), entanglement of the fibers 14 exerts markedly efficient function in improving the strength.

In this case, correspondingly high strength can be obtained when a matrix polymer having relatively high strength is used.

(19) However, no information is available to date concerning an example in which, like the case of the present invention, the matrix polymer of the system (a) is reinforced by treating it with a secondary processing for the purpose of effecting orientation of crystals (molecular chains).

The present invention is a reinforcing method [particle-reinforced+matrix-reinforced type] (c) in which, in addition to the reinforcing method of particle-reinforced type (a), the matrix polymer is reinforced by making a more dense system which is effected by allowing the crystals (molecular chains) N' to perform orientation through compression orientation and by closely attaching surfaces of the particles 15 and the matrix polymer.

That is, the present invention relates to a novel method in which the matrix polymer is physically reinforced by carrying out its secondary molding processing at a cold temperature, which has not been carried out conventionally, and to a composite system obtained by the method, both of which are evidently different from the conventional types.

(b) High Strength Implant Material

The implant material of the present invention is a composite material in which from 10 to 60% by weight of a bioceramics powder having a particle size or a size of an aggregated mass of particles of from 0.2 to 50 μm is substantially uniformly dispersed in a crystalline thermoplastic polymer which is basically degradable and absorbable in the living body, and is characterized in that it is a pressure-oriented molding in which crystals of said polymer are oriented by compression deformation and its crystallinity is from 10 to 70%.

The following describes the contents in detail.

(1) Bioceramics

Examples of the bioceramics to be used in the present invention include sintered hydroxylapatite, bioglass-based or crystallized glass-based glass for biological use, un-sintered hydroxylapatite, dicalcium phosphate, tricalcium phosphate, tetracalcium phosphate, octacalcium phosphate, calcite, diopside and the like which may be used alone or as a mixture of two or more.

Generally, the just described bioceramics are roughly divided into 1) surface bioactive ceramics and 2) bioabsorbable ceramics.

1) Surface Bioactive Bioceramics

Their examples include sintered hydroxylapatite (HA), bioglass-based bioglass, cerabital, crystallized glass-based A-W glass ceramics and the like and crystallized glass-based biobelit-1, implant-1, β-crystallized glass, diopside and the like.

2) Bioabsorbable Bioceramics

Their examples include un-sintered hydroxylapatite (un-sintered HA), dicalcium phosphate, α-tricalcium phosphate (α-TCP), β-tricalcium phosphate (β-TCP), tetracalcium phosphate (TeCP), octacalcium phosphate (OCP), dicalcium phosphate.hydrate.octacalcium phosphate (DCPD.OCP), dicalcium phosphate.anhydride.tetracalcium phosphate (DCPA.TeCP), calcite and the like.

Since these bioceramics have different degree of bioactivities and therefore exert different influences upon the speed and mode of the formation of new bones, they are used alone or as a mixture of two or more in such a manner that the necessary bioactivities can be obtained.

Of these bioceramics, un-sintered HA is one of the most effective bioabsorbable active powders to be used in the system of the present invention because, unlike the case of sintered HA, it is markedly similar to the HA in the living body, completely disappears by its absorption in the living body and has high activities, safety and actual results on its practical use.

(2) Particle Size of Bioceramics Powder

The term bioceramics powder as used herein means a general term for primary particles of bioceramics or secondary particles as their assembled (aggregated) masses.

1) In order to obtain a high strength composite material on the basis of the aforementioned reasons, a bioceramics powder having a particle size of from 0.2 to 50 μm, preferably from 1 to a little over 10 μm, as primary particles or secondary assembled (aggregated) masses is used. This range of particle size is also desirable from the viewpoint of uniformly dispersing it in a crystalline thermoplastic polymer which is degradable and absorbable in the living body.

When particle size of the bioceramics powder is close to the upper limit of 50 μm, it is desirably a size of an aggregated mass when primary particles of about a little over 10 μm are secondarily aggregated.

A case in which independent primary particle has a size of close to 50 μm is not desirable, because the resulting composite material is broken at the time of yielding.

The compression-oriented molding is finally finished into implant materials having various precise shapes by the method such as cutting work and the like.

When the particle size is large, processing of fine and precise shaped articles becomes difficult, because they will tip or split at the boundary face of powder. In consequence, it can be said that the particle size of 50 μm is the upper limit which determines preciseness of the shape of implant materials.

2) Also, the lower limit particle size of 0.2 μm corresponds for example to the size of primary particles of un-sintered HA.

In general, these fine particles assemble to form secondarily aggregated particles having a size of from several μm to a little over 10 μm. When particles of bioceramics or assembled masses thereof whose apparent average particle size is within this range are uniformly dispersed in a polymer matrix, the thus obtained system satisfies both properties of high strength and fast substitution of the implant by biological bones through its absorption. As a consequence, an implant composite material having a precise shape is obtained.

3) When such an implant material containing bioceramics is implanted in the living body, the bioceramics powder exposed on the surface binds to the peripheral biological bones directly without intermediation of fibrous connective tissues or indirectly via HA deposited on the surface, so that their initial fixation can be obtained at an early stage. This characteristic feature is desirable for the implant materials such as pins, screws and the like which are used for binding and fixing fractured bones.

Since it has binding ability to bones, it can also be applied to a plate or miscellaneous shape bone substitute or a material for osteosynthesis which could not be used in the prior art due, mainly, to the insufficient strength.

4) Implant materials which are used in bones as fractured bone fixing materials maintain the strength necessary for the fixing for 2 to 4 months at the shortest, a period required for the bones union, and then take a step in which they are deteriorated by gradual progress of hydrolysis from their surfaces where contacted with the body fluid.

During this step, the bioceramics powder contained therein is gradually exposed to the body fluid. Thereafter, the body fluid penetrates into further inside of the implant along boundary faces of the bioceramics powder and polymer. As the results, hydrolysis of the polymer and absorption of the degraded product in the living body are effected more quickly in comparison with the case of a system of the polymer alone with no bioceramics.

Also, the exposed bioceramics powder in this step accelerates infiltration of new bones and sometimes becomes a nucleus of osteogenesis to form trabecula. In some cases, the powder itself is absorbed by osteoclasts or discharged from a bone hole. In this way, invasion and substitution by biological bone into the bone hole after disappearance of the implant material are effected smoothly.

5) The process and mode of the substitution of the bone hole with biological bone by the implant material of the present invention significantly vary depending on the type of bioceramics contained therein and shape, size or content of the particles, but, since the implant material of the present invention contains smaller amount of polymer corresponding to the charged ratio of the bioceramics powder in comparison with an implant material solely made of a bioabsorbable polymer, a danger of inducing foreign body reaction and subsequent inflammatory reaction caused by large amount of polymer pieces transiently generated during the degradation process can be avoided.

This is particularly effective in the case of completely absorbable bioactive particles such as of un-sintered HA.

Also, repairing speed of bone holes can be optionally controlled by selecting suitable type, size and amount of bioceramics.

(3) Composition of Bioabsorbable Polymer Material (Polymer)

This is the same as that of the polymer material to be used in the aforementioned material for osteosynthesis which is substantially comprising a polymer.

(4) Molecular Weights of Material Polymer and Pre-molded Material

1) The aforementioned polymer requires certain physical properties, at least strength of a certain degree or more, as the material for osteosynthesis, but molecular weight of said polymer decreases at the stage of its melt molding into a pre-molded material such as a billet or the like, so that, in the case of a polylactic acid or a lactic acid-glycolic acid copolymer, it is important to use a polymer having an initial viscosity average molecular weight of from 150,000 to 700,000, preferably from 250,000 to 550,000.

When a polymer having a molecular weight within this range is used, a pre-molded material finally having a viscosity average molecular weight of from 100,000 to 600,000 (finally having a viscosity average molecular weight of from 200,000 to 500,000 when a polymer having the aforementioned preferred molecular weight range of from 250,000 to 550,000 is used) can be obtained by carrying out melt molding processing under heating condition.

2) Said polymer can be made into a composite material for use in high strength implant materials by the subsequent plastic deformation at a cold temperature for the orientation of molecular chains (crystals) by compression orientation, and reduction of the molecular weight can be prevented as small as possible when the plastic deformation step is carried out under properly set conditions.

The range of viscosity average molecular weight of the polymer which constitutes the bioceramics-containing implant material is different from the range of the case of an implant obtained by the same forming method but solely from the polymer. The reason for this is that there are differences in terms of apparent melt viscosity and degree of deterioration during the step due to the large amount of bioceramics powder contained in this system.

When a molding in which the polymer of the present invention has a molecular weight within this range and its molecular chains (crystals) are oriented by compression deformation treatment is actually used in the living body for example as a material for osteosynthesis, it maintains similar strength to that of the biological bone at least for 2 to 4 months, an average period required for bone union, and is then gradually degraded at such a rate that small pieces generated by degradation of the material for osteosynthesis do not exert strong foreign body reactions upon peripheral tissues and cells and therefore do not cause inflammatory reactions.

Since bioactive properties of bioceramics are generated in this step, initial binding with bones is obtained, and substitution with bones progresses thereafter smoothly.

3) When initial viscosity average molecular weight of the polymer is less than 150,000, high initial strength cannot be obtained, though there is an advantage in that molding can be carried out easily due to low melt viscosity. Also, the strength-maintaining period becomes shorter than the period necessary for bone union because of quick reduction of the strength in the living body. In addition, since there is a possibility in that low molecular weight small pieces are generated in a large amount within a short period of from 1.5 to 2 years after its implantation into the living body, there is a danger of inducing inflammation by their foreign body reaction.

On the other hand, when initial viscosity average molecular weight of the polymer is too large exceeding 700,000, the polymer can hardly flow at the time of heating, and high temperature and high pressure therefore are required when a pre-molded material is produced by melt molding, so that sharp reduction of its molecular weight occurs due to heat generated by high shear stress and frictional force at the time of the processing, and molecular weight of the finally obtained implant material becomes rather lower than the case in which a polymer having a molecular weight of 700,000 or less is used, thus entailing smaller strength than expected.

In the case of a polymer having a low initial viscosity average molecular weight of from 150,000 to 200,000, it is possible to charge the bioceramics powder in a relatively large amount of 30 to 60% by weight. However, since it is apt to break when yielded (yield breakage) by receiving external forces such as bending deformation and the like when the molecular weight becomes much lower after melt molding, it is desirable to control the charging amount at a low level of from 10 to 30% by weight, and it is also desirable to control the deformation degree R which will be described later at a relatively low level.

On the other hand, since it is relatively difficult to effect melt molding of a polymer having a high viscosity average molecular weight of from 550,000 to 700,000, it is more difficult to effect melt molding by charging the bioceramics powder in a large amount of from 40 to 60% by weight. In consequence, it is desirable to control amount of the bioceramics powder at a level of 20% by weight or less, and the deformation degree R (which will be described later) also to a low level inevitably.

In short, relatively broad ranges of charging amount and deformation degree R can be selected when the initial viscosity average molecular weight is approximately from 200,000 to 550,000. Also, proper strength-maintaining period in the living body and modest degradation absorption rate can be obtained by this range of molecular weight.

4) Fluidity of the mixture becomes poor when charging amount of the filler is large. Accordingly, in order to facilitate the molding by reducing melt viscosity, a low molecular weight polymer having a viscosity average molecular weight of 100,000 or less, or 10,000 or less as occasion demands, may be added as a lubricant in such a small amount that it does not exert influences upon physical properties of the final implant.

When amount of residual monomer in the polymer to be used is large, reduction of the molecular weight occur during the processing step and its degradation in the living body also becomes fast, so that it is desirable to control its amount at a level of approximately 0.5% by weight or less.

When the filler is charged in a large amount of 40% by weight or more, the filler surface may be treated with a soft bioabsorbable polymer or a complex of D form and L form optical isomers of polylactic acid, in order to improve surface binding ability between the two materials.

By the subsequent molecular (crystalline) orientation treatment by press-charging into a forming mold, a high strength compression-oriented molding, namely a material for implant use, is obtained without substantially reducing the molecular weight.

Thereafter, high strength implant materials having a desired shape such as screw, pin, rod, disc, button, cylinder or the like are produced by the secondary processing such as cutting work, slicing, punching, boring or the like.

(e) Crystallinity

When a balance between two required factors, namely high mechanical strength and appropriate hydrolysis rate, is taken into consideration, it is necessary to select crystallinity of the pressure-oriented molding of the present invention within the range of from 10 to 70%, preferably from 20 to 50%.

When the crystallinity exceeds 70%, apparent rigidity of the molding is high, but it becomes brittle due to lack in toughness and is easily broken when stress is added thereto in the living body. Also, such a high degree is not desirable, because a prolonged period of time is required for its absorption and disappearance in the living body due to its unnecessarily slow degradation.

On the other hand, improvement of its strength cannot be expected when it has a low crystallinity of less than 10%.

Thus, when initial mechanical strength of the molding and maintenance thereof and its disappearing rate by degradation and absorption or low stimulation degree in the living body are taken into consideration, appropriate crystallinity is from 10 to 70%, preferably from 20 to 50%.

Even at a low crystallinity of from 10 to 20%, the strength is improved by the effect of the filler in comparison with the case of no charging.

Also, even at a high crystallinity of from 50 to 70%, microcrystals are formed during the plastic deformation by compression so that disadvantageous influences upon the degradation and absorption in the living body do not occur frequently.

(f) Density

Since the implant material of the present invention is a three-dimensionally compression-oriented molding, its density becomes high in comparison with the prior art drawn and oriented molding. Though it varies depending on the deformation degree, the density becomes from 1.4 to 1.5 $g/cm^3$ when bioceramics are mixed in the 20% level, from 1.5 to 1.6 $g/cm^3$ when mixed in the 30% level, from 1.6 to 1.7 $g/cm^3$ when mixed in the 40% level and from 1.7 to 1.8 $g/cm^3$ when mixed in the 50% level.

This high density is also an index which shows denseness of the material and therefore is one of important factors which prove high strength.

(g) Crystal Form

Since the implant material of the present invention is produced by compression deformation orientation, crystals (molecular chains) of the molding are basically oriented in parallel with a plurality of reference axes.

In general, anisotropy in terms of the strength of molding becomes small as the number of reference axes is increased, so that breakage by relatively weak force from a certain direction, which is common in directional materials, becomes less.

The fact that crystals of the molding in the implant material of the present invention are basically oriented in parallel with a plurality of reference axes can be proved in the same manner as the aforementioned case of the material for osteosynthesis as illustratively shown in FIG. 1 and FIG. 2.

(C) [General Remarks] Production Method of Material for Osteosynthesis (a) The method for the production of the material for osteosynthesis of the present invention, namely an oriented molding having a crystal form in which crystals are basically oriented in parallel with a plurality of reference axes, basically comprises (1) a first step in which a pre-molded material is produced by melt-molding a crystalline thermoplastic polymer material which is degradable and absorbable in the living body, using an extruder or the like, (2) a second step in which an oriented molding is produced by forcing the pre-molded material (billet) into a narrow space formed by a forming mold whose bottom end is basically closed while carrying out plastic deformation at a cold temperature, thereby effecting orientation by compression deformation, or another second step in which an oriented molding is produced by forge-charging the billet into a space of a forming mold having a space which is smaller, partially or as a whole, than the diameter, thickness or width of said molding, or into a forming mold having a space which is smaller than the volume of the billet, while carrying out plastic deformation, and (3) an additional step in which a shape of object is formed by carrying out a processing such as cutting work or the like as occasion demands.

The term "cold temperature" as used herein means a temperature (Tc) at which crystallization can be effected but is lower than the conventional molding temperature which is equal to or higher than the melt temperature, namely a temperature between the glass transition temperature (Tg) and melt temperature (Tm) of the thermoplastic polymer material.

That is, when a billet having a larger diameter is forced with a pressure into the cavity of a forming mold having a smaller diameter from its upper part through a diameter-reducing part having a slope θ as shown in FIG. 4, while effecting plastic deformation at a cold temperature, the polymer having poor fluidity at Tm or below, which does not have heat fluidity like a molten polymer at the time of forced charging, undergoes plastic deformation and receives large shear caused by friction between the billet and inner side of the forming mold.

Since this shear force acts as an external force of diagonal or transverse direction which causes orientation of the polymer, molecular chains (crystals) of the polymer are oriented by the deformation along its press-charging direction into the forming mold.

That is, a form of crystals in which they are oriented in parallel with a plurality of reference axes is obtained in response to the press charging method of the billet.

In this case, anisotropy in view of physical strength becomes small as the number of orientation reference axes is increased. Under such a condition, the molding is pressurized in the diagonal or transverse direction which is the direction of forced charge, so that the molding becomes dense. As the results, an oriented molding is obtained in which anisotropy in view of physical strength is small different from the case of simple uni-axial drawing in the longitudinal axis direction, and in which mechanical properties such as bending strength, tensile strength, tear strength, shear strength, torsional strength, surface hardness and the like are generally improved with a good balance.

The thus oriented molding is made into high strength materials for osteosynthesis having various shapes as occasion demands, by carrying out final processing such as cutting work or the like to form desired shapes.

(b) Production of Pressure-oriented Molding (1) Compression Orientation Molding

This method comprises producing a pre-molded material by melt molding of the polymer material and press-charging the pre-molded material into a narrow space of a forming mold whose bottom end is basically closed, while carrying out plastic deformation at a cold temperature, thereby effecting compression orientation.

(2) Forging Orientation Molding

This method comprises producing a pre-molded material by melt molding of the polymer material and press-charging the pre-molded material continuously or discontinuously into a narrow space of a forming mold having a space which is smaller, partially or as a whole, than the sectional area, thickness or width of said molding as defined in the foregoing, or into a forming mold having a space of total volume which is smaller than the volume of the pre-molded material, while carrying out plastic deformation, thereby effecting forging orientation.

(3) Deformation Degree

When a billet is press-charged (forced compression) into the cavity of a forming mold having a sectional area which is from $2/3$ to $1/6$ of the sectional area of the billet, a deformation degree $R=S_0/S$ (wherein $S_0$ is sectional area of a billet and $S$ is sectional area of a compression-oriented molding) of the resulting oriented molding obtained by compression deformation becomes a value substantially within the range of from 1.5 to 6.0, and such a value is effective in markedly improving the strength, which will be shown later by data in the Examples.

In addition, when press-charged into a mold having partially different R values within this range (including a case in which the cross sectional area in the advancing direction of the polymer by its forced charge partially varies, and the other portions excluding such parts have the same sectional area of the billet), the orientation axes are jumbled in complicated manner and the anisotropy also does not become simple.

In a molding, orientation degree of a portion having a large R value becomes higher than that of a portion having a small R value, and mechanical strength of the former portion generally becomes large. In consequence, a molding having partially different strengths can be produced on purpose according to its use.

Such an application can be made only by the method of the present invention in which an oriented molding is produced through plastic deformation by press-charging a billet into a mold, which is a remarkable advantage of the present invention when compared with the drawing method which cannot make a portion having different draw ratio in the middle of the operation.

That is, this point is also one of the reasons that the method of the present invention which is effected by compression orientation is greatly advantageous in comparison with the prior art method effected by drawing orientation.

In this case, when the sectional area of cavity is larger than $2/3$ of the sectional area of billet, it is difficult to obtain a compression-oriented molding having strength and hardness because of small molecular chain or crystal orientation and compression ratio at the time of the press charging. On the other hand, when it is smaller than $1/6$, not only press charging of the billet into the cavity becomes difficult but also there is a possibility of causing fibrillation of the polymer. When fibrillation is generated, strength of the molding in its transverse direction is improved, but that of the longitudinal direction is reduced so that fibrils in the longitudinal direction are apt to be split by shear force.

(4) Plastic Deformation Temperature

It is desirable that the plastic deformation temperature of billet is a temperature at which crystallization can be effected (Tc) which is between the glass transition temperature (Tg) and melt temperature (Tm) of the thermoplastic polymer material.

Illustratively, in the case of a polylactic acid or a lactic acid-glycolic acid copolymer, it is within the range of from 60 to 160° C., preferably from 80 to 110° C., as will be shown later in Examples.

When a billet is press-charged into the cavity at this temperature, the press charging becomes relatively easy, orientation of molecular chains (crystals) can be made efficiently and crystallinity can be controlled at will.

In doing this, it is necessary to select a proper rate (for example, from 8 to 80 mm/minute) in order to prevent a stick slip phenomenon during the press charging step.

(5) In the case of orientation molding by compression deformation, either by compression orientation molding or forging orientation molding, friction occurs between a billet and the surface of the forming mold when the billet is press-charged into the forming mold while effecting plastic deformation under an appropriate high pressure (for example, from 100 to 4,000 $kg/cm^2$, preferably from 200 to 2,500 $kg/cm^2$) at a cold temperature (the aforementioned temperature at which crystallization can be effected (Tc) which is between the glass transition temperature (Tg) and melt temperature (Tm) of the polymer material, for example, in the case of a polylactic acid or a lactic acid-glycolic acid copolymer, from 60 to 160° C., preferably from 80 to 110° C.), and the friction acts as an external force in the transverse or diagonal direction for the orientation of the polymer, thereby forming a structure of crystals in which they are oriented in parallel with a large number of reference axes.

At this stage, the molding is pressurized in the machine direction and becomes dense in terms of its quality, and density of the material for osteosynthesis becomes high, so that high strength is obtained as the result.

(D) [Discussion of Details] Production Method of Material for Osteosynthesis

This method is described further illustratively based on the drawings.

FIG. 4 is a sectional view showing conditions of orientation molding by compression deformation, before press charging of a billet into the cavity of a forming mold.

FIG. 5 is a sectional view showing conditions of orientation molding by compression deformation, after press charging of a billet into the cavity of a forming mold.

FIG. 6 is an elevation view showing an example of screw for osteosynthesis obtained by a final cutting work.

The production method of the present invention is described in the case of the production of the screw for osteosynthesis 30 shown in FIG. 6. This method basically comprises the following three steps.

(i) A primary molding step in which a pre-molded material, for example a thick columnar billet 1, is produced by melt molding of a crystalline thermoplastic polymer which is degradable and absorbable in the living body, (ii) a secondary molding step in which, as shown in FIG. 4, the billet 1 is put into a container cylinder part 2a of a forming mold 2 and the billet 1 is continuously or intermittently pressurized by a piston (ram) or the like compression means 2b and then, as showing FIG. 5, the billet 1 is made into a thin columnar compression-oriented molding 10 by press charging it into a cavity 2c of the forming mold 2 while effecting plastic deformation at a cold temperature, and (iii) a processing step in which the compression-oriented molding 10 released from the forming mold 2 is cut into the screw for osteosynthesis 30 shown in FIG. 6.

(a) Melt Molding

Melt extrusion molding may be used preferably as the method for melt molding the billet 1 from a polymer material in the primary molding step, but other molding methods such as injection molding, press molding and the like may also be employed when prevention of molecular weight reduction is taken into consideration.

When melt extrusion molding is employed, it is important to use a temperature condition which is slightly higher than the melting point of the polymer material and a minimum pressure condition under which the extrusion can be effected, in order to prevent reduction of molecular weight of the polymer material as low as possible.

For example, when the polymer material is poly L-lactic acid (PLLA) having a viscosity average molecular weight of approximately from 200,000 to 600,000, it is desirable to employ a temperature condition within the range of from equal to or higher than its melting temperature to equal to or lower than 220° C., preferably to 200° C. or less, and a pressure condition of approximately 260 $kg/cm^2$ or less, preferably from 170 to 210 $kg/cm^2$.

(b) Compression Orientation Molding

As exemplified in FIGS. 4 and 5 as orientation molding by compression deformation, it is desirable to carry out melt molding of the billet 1 in such a manner that its sectional shape becomes close to the sectional shape of the cavity 2c of the forming mold 2. When the cavity 2c has a circular sectional shape like the case of the present invention, it is desirable to carry out melt molding of the billet 1 in such a manner that it becomes a columnar article having more larger circular sectional shape.

When sectional shape of the billet 1 becomes similar to the sectional shape of the cavity 2c, the billet 1 can be press-charged into the cavity 2c by effecting its plastic deformation by uniform compression from its peripheral, so that it becomes possible to obtain the compression-oriented molding 10 having uniform deformation degree.

However, the sectional shape of billet is not particularly limited to the circular form, and other irregular shapes (e.g., polygonal and the like) can also be employed as a matter of course, with the proviso that these shapes correspond to the shapes of oriented moldings obtained through compression deformation by the subsequent compression molding or forging molding.

Also, it is desirable that the sectional area of billet 1 is from 1.5 to 6.0 times larger than the sectional area of cavity 2c. That is, when said billet 1 is press-charged into the cavity 2c having a sectional area which is from ⅔ to ⅙ of the sectional area of the billet 1, it can be processed into a compression-oriented molding 10 having a deformation degree $R=S_0/S$ (wherein $S_0$ is sectional area of the billet 1 and S is sectional area of the compression-oriented molding 10) of from 1.5 to 6.0.

In this way, strength and hardness of the compression-oriented molding 10 are significantly improved as will be shown later by data in Examples. By further processing this by the means such as cutting, screw cutting, slicing and the like, ideal materials for osteosynthesis, such as the materials for osteosynthesis (e.g., screws, nails, pins, plates and the like) can be obtained.

When the billet 1 is press-charged into a cavity 2c whose sectional area is larger than ⅔ of that of the billet 1, it becomes difficult to obtain a compression-oriented molding 10 having high strength and hardness due to low orientation and compression ratio of molecular chains or crystals.

On the other hand, it is difficult to press charge the billet into a cavity 2c whose sectional area is smaller than ⅙ of that of the billet, and, even if it could be made, fibrillation would occur due to too much orientation of the polymer, thus entailing aptness to generate cracks between fibrils.

Next, the following describes the mold to be used in the orientation molding by compression deformation, the orientation mechanism and methods thereof.

FIG. 4 is a sectional view showing conditions of orientation molding by compression deformation, before press charging of a billet into the cavity of a forming mold.

(1) As shown in FIG. 4, the forming mold 2 to be used in the secondary molding step is constructed in such a manner that the container cylinder part 2a in a thick cylindrical shape where the billet 1 is contained is connected with the molding cavity 2c in a thin cylindrical shape where the billet 1 is press-charged by the compression means 2b, vertically on the same axis via the diameter-reducing part 20a having a downward taper.

The upper part of the container cylinder part 2a is equipped with the compression means 2b, such as a piston (ram) or the like, which pressurizes the billet 1 continuously or intermittently. In addition, extremely small air vent pores or gaps are formed on the bottom part of the cavity 2c (not shown in the drawing).

(2) Based on the aforementioned reasons, the radius $r_1$ of the container cylinder part 2a and the radius $r_2$ of the cavity 2c are set in such values that an inequality: $1.5 \leq (r_1/r_2)^2 \leq 6.0$ is realized, so that the columnar billet 1 having a sectional area from 1.5 to 6.0 times larger than the sectional area of cavity 2c can be contained in the container cylinder part 2a.

(3) Also, the angle of inclination θ of the taper of diameter-reducing part 20a is set within the range of from 10 to 60°.

When the angle of inclination θ is smaller than 10°, pressure for the press charging of the billet 1 into the cavity 2c cannot be increased, and orientation of molecular chains (crystals) of the resulting compression-oriented molding 10 (not shown in the drawing) becomes low, so that high strength cannot be obtained.

On the other hand, when the angle of inclination θ is larger than 60°, the press charging becomes difficult. In consequence, it is desirable to set the angle of inclination θ to from 10° to 60°, preferably from 15° to 45°.

In addition, when the angle of inclination θ is set to smaller level as the value of $(r_1/r_2)^2$ becomes closer to 6.0 within the range of from 1.5 to 6.0, the press charging operation can be made easily and a uniform molding can be obtained easily, so that such a setting is desirable.

(4) As shown in FIG. 5, when the billet 1 is contained in the container cylinder part 2a using such a type of forming mold 2 and press-charged into the cavity 2c by continuously or intermittently pressurizing the billet 1 with the compression means 2b while effecting plastic deformation at a cold temperature, large shear forces are generated at the time of the press charging by its friction with the inner surface of diameter-reducing part 20a and with the inner surface of cavity 2c, and such forces act as external forces (vector forces) of transverse and diagonal directions to effect orientation of the polymer.

Accordingly, the polymer is basically orientated to accelerate crystallization along the inner surface of diameter-reducing part 20a, and, since the press charging into the central part of the molding cavity 2c has preference to that into the peripheral part, crystal axis of the compression-oriented molding 10 molded in the shape of the cavity 2c is oriented in the diagonal direction against its vertical direction axis line in response to the angle of inclination θ of the taper of the diameter-reducing part.

(5) It is considered that the compression-oriented molding 1 obtained in this manner is oriented in a concentric fashion along the inner surface of cavity 2c and has a large number of reference axes. Since the polymer is compressed in the vertical direction (mechanical direction) at the same time, a qualitatively dense compression-oriented molding 10 having a thin and columnar shape is obtained.

In that case, the orientation angle of crystals (angle of crystals to an axis which becomes the mechanical core of the compression-oriented molding) is approximately decided by the angle of inclination θ of the diameter-reducing part 20a and the area ratio of the cross section of the container cylinder part 2a to that of the cavity 2c.

That is, as shown in FIG. 8, when the radius of the container cylinder part 2a is defined as $r_1$, and the radius of the cavity 2c as $r_2$, the angle of inclination of the diameter-reducing part 20a to the central axis Lc of the forming mold 2 as θ, and the area ratio of the cross section of the container cylinder part 2a to that of the cavity 2c as $A=r_1^2/r_2^2$, and when D is defined as a press-charged distance of a point Y on the central axis Lc during a point X on the peripheral surface of the billet 1 is press-charged in a distance d toward the axis Lc along the inner surface of the taper, it is considered that the crystals are oriented in the direction of the line segment Lm. When the orientation angle of crystals oriented toward the line segment Lm (angle to the axis Lc) is defined as θm, an expression tan θm=$r_2$/(D−d) is obtained, and, since D−d=A·d, the expression becomes $$\tan \theta m = r_2/A \cdot d \quad \text{[formula 1]}.$$

Since d=$(r_1-r_2)$/tan θ, its substitution for the [formula 1] yields $$\tan \theta m = r_2 \tan \theta/[A(r_1-r_2)] \quad \text{[formula 2]},$$

and since $r_1=r_2 \cdot A^{0.5}$, its substitution for the [formula 2] yields $$\tan \theta m = \tan \theta/[A \cdot (A^{0.5}-1)] \quad \text{[formula 3]}$$

(6) In consequence, the crystals are oriented in the diagonal direction to the axis at the orientation angle θm realized by the [formula 3], so that the orientation angle θm of crystals becomes large as the angle of inclination θ of the taper inner surface becomes large, and the orientation angle of crystals becomes small as the area ratio A of the cross section of the container cylinder part 2a to that of the cavity 2c becomes large. Thus, the crystals can be adjusted to desired orientation angle θm by changing the angle of inclination θ and the area ratio A.

(7) As described in the foregoing, the compression-oriented molding 10 having a crystal form in which crystals are oriented in parallel with a large number of reference axes has small anisotropy in terms of strength and is dense in quality in comparison with a molding obtained by simple uni-axial drawing in the longitudinal axis direction, so that the mechanical properties such as bending strength, bending modulus, compression strength, tensile strength, tear strength, shear strength, torsional strength, surface hardness and the like are improved, and its breakage hardly occurs as the results.

Particularly, when deformation degree R of the compression-oriented molding 10 is within the range of from 1.5 to 6.0, improvement of its strength becomes significant; for example, the compression-oriented molding 10 having the just described degree of deformation obtained by press-charging a polylactic acid billet 1 (viscosity average molecular weight: from 100,000 to 400,000) has a bending strength of from 160 to 300 MPa, and the physical strengths such as bending strength, torsional strength, surface hardness and the like are larger in general than those of a drawn article obtained by uni-axially drawing polylactic acid at a draw ratio as substantially the same deformation degree of the above-described deformation ratio.

(8) Contrary to this, in the case of the free width uni-axial drawing in which a billet of a polymer material is drawn in the longitudinal axis direction, external forces are not added in the transverse direction (from sides), so that thickness of the molding becomes thin during the drawing step. Also, since it is drawn in the longitudinal axis direction which is the orientation axis, the molding becomes dilute in quality.

In consequence, when compared with the compression-oriented molding 10 having a crystal form in which crystals are basically oriented in parallel with a large number of reference axes, this molding obtained by drawing has large anisotropy and its mechanical strengths are also small in general.

(9) Press charging of the billet 1 may be carried out at a temperature lower than the glass transition temperature (Tg) depending on the kind of polymer material, but, when easy press charging, effects of orientation of molecular chains (crystals), adjustment of crystallinity and the like are taken into consideration, it is desirable to press-charge the billet 1 into the cavity 2c by heating it in the container cylinder part 2a at a crystallizable temperature (Tc) between its glass transition temperature (Tg) and melt temperature (Tm).

This temperature for effecting plastic deformation by press charging is from 60 to 160° C., preferably from 80 to 110° C. in the case of the aforementioned polylactic acid billet 1.

(10) Also, the press charging pressure is from 100 to 4,000 kg/cm$^2$, preferably from 200 to 2,500 kg/cm$^2$.

When the press charging is carried out under an extreme pressure of exceeding 4,000 kg/cm$^2$, the molecular weight is sharply reduced due to shear force and heat generated thereby, so that it rather becomes difficult to obtain the compression-oriented molding 10 having high strength. Also, when the press charging pressure is less than 100 kg/cm$^2$, it is difficult to press-charge the billet 1 into the cavity 2c having a sectional area of smaller than $\frac{2}{3}$, so that a compression-oriented molding having large strength and hardness cannot be obtained.

(11) The press charging rate may be from 8 to 800 mm/minute, preferably from 40 to 60 mm/minute, when a generally used forming mold is used or a special surface treatment is not applied in order to improve slipping on the metal surface.

When press-charged at a rate slower than 8 mm/minute, a portion of the billet 1 not yet press-charged into the cavity 2c during its press charging is hardened by the progress of crystallization, so that the press charging becomes difficult. On the other hand, when press-charged at a rate quicker than 80 mm/minute, stick slip occurs and the molding becomes irregular, so that such a rate is not desirable.

Crystallinity of the compression-oriented molding 10 obtained in the aforementioned manner by press-charging the billet 1 into the cavity 2c changes depending on the deformation degree R of said molding 10 and temperature, pressure, time (press charging rate) and the like at the time of the press charging, and the crystallinity generally becomes high as the deformation degree R becomes high, the temperature becomes high, the pressure becomes high and the time becomes long.

(12) It is desirable that crystallinity of the compression-oriented molding 10 is within the range of from 30 to 60%, preferably from 40 to 50%.

Since screws and the materials for osteosynthesis obtained by applying processing such as cutting work and the like to the compression-oriented molding 10 having such a range of crystallinity have proper balance in terms of the ratio of crystalline phase to amorphous phase of the polymer, the improvement of strength and hardness due to the crystalline phase is well harmonized with the flexibility due to the amorphous phase, so that the brittleness which is common in the case of crystalline phase alone is not generated and the soft and weak property having no strength which is common in the case of amorphous phase alone is also not generated. Accordingly, the molding becomes a material for osteosynthesis having toughness and sufficiently high strengths in general.

When the crystallinity is less than 30%, improvement of strength by crystals cannot generally be expected.

On the other hand, strength is improved as the crystallinity increases, but a brittle property of easily causing breakage when impact and the like are added is generated considerably due to lack in toughness when the crystallinity becomes higher than 60%.

In addition, it is known generally that crystallinity of the polymer material to be used in the present invention gradually increases during a step in which the polymer is changed into small molecules as its hydrolysis progresses in the living body, and the progress of hydrolysis is reduced as the crystallinity increases, so that its hydrolysis into molecules small enough to be absorbed by the living body cannot easily-be effected, but, when the polymer has the aforementioned crystallinity of from 30 to 60%, its possibility of causing reduced hydrolysis rate in the living body is not so great, because the hydrolysate is simultaneously changed into more smaller pieces in the living body by external forces from outside the living body.

From these reasons, it is desirable to adjust crystallinity of the compression-oriented molding 10 to from 30 to 60% by controlling deformation degree R of the compression-oriented molding 10 and temperature, pressure, time and the like at the time of press charging within the aforementioned ranges or by carrying out a short time heating treatment at a crystallization temperature (for example, at a temperature of from 90 to 160° C.) after the press charging.

(13) When press charging of the billet 1 is finished, the compression-oriented molding 10 is cooled and released from the forming mold 2, the un-oriented margin material part 10a of the compression-oriented molding 10 is cut out and then the resulting article is subjected to processes such as cutting, screw cutting, slicing and the like to obtain a screw for osteosynthesis 30 equipped with a screw axis part 31, a screw head part 32 and a rotating jig insertion hole 33 as shown in FIG. 6.

The screw for osteosynthesis may have various shapes other than the shape shown in FIG. 6 and, as a matter of course, the molding may be processed into various desired materials for osteosynthesis other than screws, such as pins, nails, buttons, cylindrical products and the like, by the means such as cutting, screw cutting, boring, slicing and the like.

In this connection, the aforementioned means (e.g., cutting work and the like) are not required when the thin, columnar compression-oriented molding 10 obtained after cutting out the margin material part 10a is used directly as a rod for osteosynthesis.

Since the screw for osteosynthesis 30 produced in the aforementioned manner is a product obtained by processing (e.g., cutting work and the like) of a dense compression-oriented molding 10 (viscosity average molecular weight; from 100,000 to 400,000, crystallinity: from 30 to 60%) having a crystal form in which crystals are basically oriented in parallel with a large number of reference axis and a deformation degree R of from 1.5 to 6.0, the screw has small anisotropy in view of strength and is excellent in the mechanical properties such as bending strength, bending modulus, compression strength, tensile strength, tear strength, shear strength, torsional strength, surface hardness and the like in comparison with the prior art uni-axially drawn materials for osteosynthesis, and, being proper in its hydrolysis resistance, it maintains its strength similar to that of biological bones in the living body for 2 to 4 months which are necessary for bone union and is gradually degraded and absorbed thereafter at such an appropriate degradation rate that it does not cause inflammatory reactions, so that it is an almost ideal implant material.

(14) In the aforementioned mode of practice, a mold constructed by vertically connecting the container cylinder part 2a in a cylindrical shape having a large radius with the cavity 2c in a cylindrical shape having a small radius, via the diameter-reducing part 20a in a downward conical shape having a taper with the same angle of inclination θ around whole peripheral, is used as the forming mold 2.

However, when a plate-shaped material for osteosynthesis such as a plate for osteosynthesis is produced, it may be effected by the use of a forming mold in which a container cylinder part having a rectangular section is connected with a cavity having a similar but smaller rectangular section via a diameter-reducing part.

In that case, a plate-shaped molding diagonally oriented from four sides toward the vertical axis is obtained when taper of the diameter-reducing part is arranged on four sides, but a plate-shaped molding diagonally oriented from both sides toward the vertical axis-containing face is obtained when taper of the diameter-reducing part is arranged on only two sides of the longitudinal direction.

(15) Though the angle of inclination θ of the diameter-reducing part 20a is fixed in the aforementioned mode of practice of the columnar article, the axis L which becomes the mechanical core of the molding or the face M which contains said axis L is dislocated from the center when the angle is changed over the whole peripheral or partially or when the angle of inclination θ of two sides of the longitudinal direction of a prismatic molding is changed, so that the orientation occurs diagonally toward the dislocated axis L or face M.

For example, as shown in FIG. 9, when a rectangular compression-molded molding is formed from the rectangular billet 1 having a large sectional area by compression molding using the forming mold 2 in which the diameter-reducing part 20a has different angles of inclination $\theta_1$ and $\theta_2$ ($\theta_1 < \theta_2$) on the left and right sides, an oriented molding in which the face M is dislocated to the right side is obtained.

As shown in FIG. 10, crystals of this oriented molding are oriented in parallel with the reference axes N and N' diagonally slanted from both sides toward the face M which is dislocated to the right side.

Since this compression-oriented molding has different angles of orientation of crystals at the left and right sides, it becomes a plate-shaped molding having different strengths at both sides and can therefore be used suitably when a material for osteosynthesis having different strength at both sides is required.

Since the strengths of both sides can be deflected by dislocating the position of face M through various changes in the angle of inclination θ, they can be adjusted at will in response to respective uses.

As described above, types of the forming mold can be selected in response to respective shapes of the materials for osteosynthesis to be produced and their applications.

(c) Forging Orientation Molding

FIG. 7 is a sectional view showing conditions before press charging of billet 1 into cavity 2c of forming mold 2, in a forging orientation molding as another mode of the present invention.

(1) In the forming mold to be used in this mode of practice, a container cylinder part 2a in a cylindrical or (poly)angular cylindrical shape is arranged on the central part of a cavity 2c in a hollow disc or hollow (poly)angular board shape (heteromorphic shape) having a project area larger than the sectional area of said cylinder part 2a, and a piston (ram) or the like compression means 2b is arranged on the upper part of the container cylinder part 2a.

In this case, it is a basic condition that the thickness of cavity 2c (area of cross section in the press charge direction) is smaller than the diameter of container cylinder part 2a (area of cross section). The reason for this is that the forging method also aims at effecting crystal orientation by pressurization.

Such a condition may be satisfied over entire portion or a part of the cavity 2c. In order to charge the material to be formed into every space of the cavity 2c, the volume of billet 1 must be larger than the volume of cavity 2c.

Particularly, when this condition is satisfied partially (at a partial part) (in other words, in the case of a molding which have a part where the thickness (diameter) of cavity 2c is partly larger than the diameter of billet 1 and the other parts are smaller than or equal to the latter diameter), the volume of billet 1 must be considerably larger than the total volume of the cavity, in order to effect press charging of the material into every space of the mold.

(2) In the mode of practice shown in FIG. 7, the billet 1 obtained from a polymer material by its melt molding into a cylindrical or (poly)angular cylindrical shape (heteromorphic shape) whose sectional shape is identical to the sectional shape of container cylinder part 2a and whose volume is larger than the volume of cavity 2c is contained in the container cylinder part 2a and pressurized continuously or intermittently with the compression means 2b, thereby effecting press charging of the billet 1 by its beating and flaring from the central part of the cavity 2c having a large projected plane area toward its peripheral parts at a cold temperature, so that a forging-oriented molding having a disc or (poly)angular board shape (polymorphic shape) can be obtained.

Unlike the case of the aforementioned compression-oriented molding, the forging-oriented molding obtained by this mode is a forging-oriented molding in which molecular chains and crystals are oriented from the central part of the forming cavity 2c toward its peripheral parts with a large number of axes in the radial direction, basically orienting in parallel with a large number of reference axes. Therefore, this is a molding having an orientation form which is evidently different from that of a simply uni-axially drawn product.

(3) Such a mode of method is particularly effective for the production of materials for osteosynthesis in the a shape such as cylinder, (poly)angular board, button, or the like having holes therein or of heteromorphic plate-shaped bone prosthetic materials (bone fillers) having partially different thickness.

(4) The cavity 2d shown in FIG. 7 with broken lines shows an example in which the R value gradually increases as the cavity approaches its tip end. That is, this is an example in which the same molding has portions where the R value changes within the range of from ⅔ to ⅙.

In this case, the orientation axis forms a condition in which it cuts into the thickness direction (toward the bottom part) as it reaches the tip end of the cavity 2d, so that the resulting product becomes a molding having a complex orientation form in which this condition is mutually entangled with the aforementioned radially oriented condition from the central part of the forming cavity 2c toward its peripheral parts.

(5) The various conditions described in the case of the compression orientation molding (b) can also be employed in the forging orientation molding (c).

(E) Production of Implant Material

The method for the production of implant material of the present invention basically comprises the steps of (a) preparing in advance a mixture in which a bioceramics powder is substantially uniformly mixed with and dispersed in a biodegradable and bioabsorbable crystalline thermoplastic polymer, (b) subsequently producing a pre-molded material (e.g., a billet) by melt molding of said mixture and then (c) making said pre-molded material into a compression-oriented molding through its plastic deformation at a cold temperature by press-charging said pre-molded material into the cavity of a closed type forming mold having a narrow space whose bottom part is basically closed (in the case of compression orientation) or by press-charging it into a narrow space of a forming mold whose thickness or width of sectional area is partially or entirely smaller than that of the pre-molded material or into the cavity of a forming mold whose space is smaller than the space for containing the pre-molded material (in the case of forging orientation).

(a) Preparation of a Mixture of a Polymer and a Bioceramics Powder (1) In order to effect substantially uniform mixing and dispersion of a bioceramics powder which causes aggregation relatively easily in a matrix polymer, it is desirable to employ a method in which the bioceramics powder is thoroughly dispersed in the matrix polymer dissolved in a solvent such as dichloromethane, chloroform or the like, and the dispersion system is precipitated and made into a mixture by adding a non-solvent such as ethanol, methanol or the like.

In this case, the concentration of the dissolved polymer and the ratio of solvent to non-solvent may be decided according to the type and polymerization degree of the polymer.

(2) The bioceramics powder/matrix polymer mixing ratio is from 10% by weight to 60% by weight, preferably from 20 to 50% by weight, more preferably from 30 to 40% by weight.

When the mixing ratio is less than 10% by weight, volumetric ratio of the bioceramics powder is small, so that properties to be expected by the bioceramics, such as direct bonding to bones, bone conduction and bone induction, are not easily expressed, and substitution by the biological bones is also relatively slow similar to the case of the polymer alone.

Also, when the ratio exceeds 60% by weight, molding cannot easily be effected because of insufficient fluidity of the mixture system at the time of thermoforming and, since proper binder effect is not obtained due to insufficient amount of the polymer in the molding, the filler and polymer are apt to be separated and the product becomes brittle from the viewpoint of strength.

Also, since exposure of the bioceramics powder from the surface of the material for osteosynthesis occurs quickly during its degradation step in the living body, it is possible to cause generation of toxicity to the living body.

When the mixing ratio is within this range, desirable characteristics of both the bioceramics powder and polymer matrix are markedly expressed from both viewpoints of structure and function of the composite material.

(b) Melt Molding (1) Though the composite material of the present invention belongs to particle-reinforced composite materials, a polymer system which contains a large amount of a bioceramics powder, such as the case of the implant material of the present invention, is generally poor in fluidity, so that it is difficult to carry out thermoforming.

Since it is necessary to consider safety of the implant to the living body, it is much more difficult to carry out the forming under the present situation in that a titanium coupling agent which is markedly effective in improving fluidity cannot be used.

When such a composite material having poor fluidity is thermo-formed by a means such as general extrusion molding or the like in which shear force is added at the time of kneading and melting, the polymer itself performs deformation flow with its original flow characteristics, but, since the charged bioceramics powder does not have a property to flow by plasticizing with heat, voids are formed due to cleavage on the surface of the polymer and bioceramics particles at the time of flow deformation transfer by the forming, so that a molding having rough density is produced as the results, and a tendency to reduce strength of the molding cannot be avoided.

(2) When a polymer system which contains a large amount of a filler such as a bioceramics powder or the like is subjected to a primary molding (production of a pre-molded material by melt molding) like the case of the present invention, a ram (plunger) type melt extrusion molding is advantageous, but it is also effective to use a special type of compression molding method such as injection molding, compression molding or the like in which the aforementioned problem of generating voids is taken into consideration.

That is, the melt molding for the production of a billet can be carried out at a temperature condition of the melting point or more of the polymer, but its molecular weight is considerably reduced when the temperature is too high, so that it is desirable to carry out the melt molding at a temperature slightly higher than the melting point to prevent heat deterioration and generation of voids.

For example, when the aforementioned polylactic acid having an initial viscosity average molecular weight of approximately from 150,000 to 700,000 is used as the polymer, its viscosity average molecular weight after the melt molding can be maintained at a level of from 100,000 to 600,000, by selecting a temperature condition between its melting point and 200° C., preferably about 190° C., and carrying out thorough removal of water and drying of the polymer in advance.

In the same manner, in order to prevent reduction of molecular weight due to heat generated by friction, it is desirable to employ a pressure condition which is a minimum pressure capable of performing the melt molding, for example 300 kg/cm$^2$ or less, preferably from 150 to 250 kg/cm$^2$.

However, these conditions may be changed according to each situation, because they vary significantly depending on the composition, size (thickness, diameter, length) and the like of the pre-molded material (billet).

(3) It is desirable to carry out melt molding of the billet in such a manner that its sectional shape becomes similar to the sectional shape of the cavity of a mold for use in the compression orientation molding, and, when the cavity has a circular sectional shape, the billet is melt-molded in such a manner that it becomes a columnar shape having more larger circular sectional shape.

When the billet has a sectional shape similar to the sectional shape of the cavity, the billet can be press-charged into the cavity by effecting its plastic deformation with uniform compression from the peripheral, so that a uniform compression-oriented molding can be obtained.

(4) In that case, it is desirable to carry out the melt molding under such a condition that sectional area of the billet becomes from 1.5 to 5.0 times larger than the sectional area of the cavity. When sectional area of the billet is smaller than 1.5 times of the sectional area of the cavity, it is difficult to obtain a compression-oriented molding having large strength and hardness because of the low compression ratio of orientation of molecular chains and crystals at the time of its press charging, and, when its sectional area is larger than 5.0 times of the sectional area of the cavity, it is difficult to effect its press charging, and, even if it could be made, it would cause fibrillation and easy cracking between fibrils because of excess orientation of the polymer.

After completion of the secondary step by compression orientation in this way, a desired shape is cut out by a tertiary processing such as cutting work or the like.

(5) In some cases (particularly in the case of complex sectional shapes), a billet as the pre-molded material may be subjected to a cutting work to make it into a desired shape suitable for the next step secondary molding by a pressure orientation such as forging orientation or compression orientation.

(c) Pressure Molding in a Closed Type Mold

A molding oriented along multiple axes can be obtained by subjecting a billet as the primary molding to pressure molding using a closed type mold for secondary molding use.

With regard to the secondary molding step, deformation degree, plastic deformation temperature, plastic deformation pressure, action of pressure orientation and the like of (1) compression molding and (2) forging molding are similar to the various conditions described in the foregoing in relation to the production method of materials for osteosynthesis.

According to the method such as (1) compression molding or (2) forging molding, external forces at the time of orientation molding act in the inward direction toward the material itself, which is the opposite direction of drawing, so that the material becomes a dense state.

Accordingly, the surface between bioceramics particles and matrix polymer is changed into a closer state, and even the microscopic voids formed in the mixing step via air presented in the surface disappear, so that a high denseness is obtained. In other words, both materials become more integrally bonded structure.

In addition to the above, since the molecular chain axis and crystal phase are oriented in the matrix polymer, the resulting composite material shows markedly high strength.

Since its mode can be shown by the aforementioned illustration [particle-reinforced +matrix-reinforced type] (c) of FIG. 15, this mode is evidently different from the prior art reinforcing method by compounding of materials.

When a billet is formed by pressure orientation, crystallization progresses at the time of orientation during the molding step. The crystallinity varies depending on the molding time and temperature, and, in the case of a composite material which contains a large amount of a bioceramics powder as a filler like the case of the present invention, growth of matrix polymer crystals is inhibited by the bioceramics and the crystals are apt to be broken in pieces by the pressure at the time of plastic deformation, so that the crystallinity becomes slightly smaller than that of a case in which matrix polymer alone is molded for the same orientation. This is a desirable phenomenon from the viewpoint of the degradation rate and tissue reaction in the living body.

(F) Characteristics such as Physical Properties and the like of Implant Material (a) The pressure-oriented molding of the present invention is dense due to compression by pressure at the time of molding, and its anisotropy in view of strength is also reduced as the number of reference axes along which the crystals are oriented is increased.

On the other hand, when the reference axis is uni-axial, crystals (molecular chains) are oriented evenly in parallel with the reference axis direction.

Accordingly, breakage of the pressure-oriented molding of the present invention hardly occurs due to well-balanced mechanical properties such as bending strength, bending modulus, tensile strength, tear strength, shear strength, torsional strength, surface hardness and the like.

(b) Physical Properties

The implant material of the present invention having a bending strength of 150 to 320 MPa and a bending modulus of 6 to 15 GPa is obtained depending on the charging amount of bioceramics, deformation degree and molecular weight.

With regard to other physical strengths, a material having a tensile strength of from 80 to 180 MPa, a shear strength of from 100 to 150 MPa and a compression strength of from 100 to 150 MPa can be obtained, and these values are similar to the strengths of human cortical bones in general and stronger than those of human cortical bones synthetically, so that it can be said that it is close to the ideal as implants.

For example, when a mixture prepared by uniformly mixing and dispersing 30% by weight of HA having an average particle size of 5 $\mu$m in a homopolymer of L-lactic acid having the aforementioned range of initial viscosity average molecular weight is subjected to melt molding, and the thus obtained billet is then subjected to orientation molding by pressure deformation at a cold temperature under such a condition that the deformation degree $R=S_0/S$ becomes 1.5 or more, a pressure-oriented molding having a bending strength of 250 MPa or more is obtained, which sufficiently exceeds the bending strength of cortical bones.

When the deformation degree R which changes the degree of orientation is enlarged, mechanical strength of the composite material in the machine direction is improved. Also, when charging amount of the bioceramics powder is increased at the same time, a product having high bending modulus is obtained.

In this way, implant materials having a bending strength exceeding 300 MPa and a bending modulus close to the value 15 GPa of cortical bones can be obtained.

Because the unit is GPa, someone may consider that the range of from 6 to 15 GPa in bending modulus is not great difference from the numerical point of view. However, when the value is about 10 GPa or more, it causes great differences when compared with a value lower than the just described level, in terms of a resistance to bend or deflect at the time of insertion, a resistance in deforming a plate or rigidity thereof, when applied to practical use, so that differences more than the numerical value are found in terms of physical usefulness when it is used for example as a material for osteosynthesis.

(c) Implants for medical use can be obtained from the pressure-oriented, high strength composite molding of the present invention in the shape of a rod or the like, by further cutting it into a final molding by means of a processing such as cutting work or the like.

(d) Characteristics of Implant Material

The implant material of the present invention has the following characteristics.

(i) Since it contains fine particles of from 0.2 to 50 $\mu$m in size or assembled masses thereof (clusters) in a large amount of from 10 to 60% by weight and in a uniform state, a large number of bioceramics particles are exposed on the surface after its scraping by the means such as cutting work or the like, so that it shows excellent biological compatibility and the bioceramics bind directly to the biological bones at an early stage after its implanting, and the initial fixing ability increases as the results.

(ii) Since it is produced by a novel composite reinforcing method which reinforces the material by a polymer matrix in which molecular chains or crystals of a polymer having appropriate molecular weight and a distribution thereof are oriented and also by bioceramics, it can be designed in such a manner that high initial strength is added thereto, almost the same level of the strength is maintained at least for 2 to 4 months required for the bone union and it is gradually degraded thereafter at a rate which does not cause tissue reactions.

(iii) Since the bioceramics powder is present continuously into the inside of the composite material, the powder is exposed on the surface of the material by gradual degradation and thereby contributes to the binding of the material to biological bones.

Also, since the bioceramics powder enhances bone induction and bone conduction and finally fills up a cavity formed after disappearance of the polymer quickly, substitution of biological bones is made efficiently.

(iv) Since bioceramics fine particles are contained in the composite material in a large amount, appropriate pictures can be taken by a simple X-ray photographing, so that X-ray observation of the condition and process of therapeutic treatment can be made effectively, which is impossible in the case of a polymer alone.

In addition to the above, the matrix polymer and bioceramics have actual results of their practical use in the clinical field, are safe for the living body and have excellent biocompatibility. In consequence, it can be said that this composite material for implant use is one of ideal biomaterials.

BRIEF DESCRIPTION OF THE DRAWINGS

FIG. 1 is a schematic illustration showing orientation conditions of a columnar material for osteosynthesis.

FIG. 2 is a schematic illustration showing orientation conditions of a plate-like material for osteosynthesis.

FIG. 3(A) shows orientation conditions when an axis or face which becomes the mechanical core is located on the central position or a position having the same distance from both sides, FIG. 3(B) shows a case in which the aforementioned axis or face is dislocated from the central position or a position having the same distance from both sides, FIG. 3(C) shows a case in which the aforementioned axis is completely dislocated, and FIG. 3(D) shows orientation conditions of a usual uni-axially drawn molding.

FIG. 10 is a schematic illustration showing orientation conditions of crystals of a plate-like material for osteosynthesis.

DESCRIPTION OF MARKS

Figure 1A:
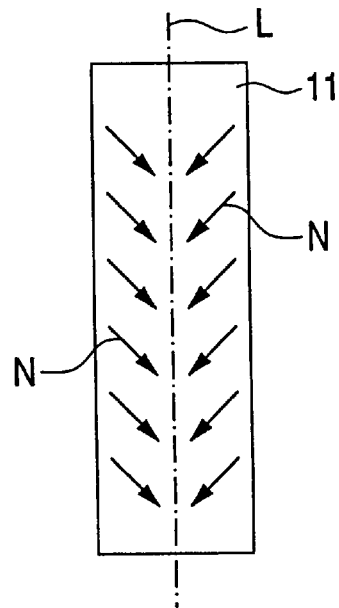
FIG. 1(A) shows orientation conditions of a longitudinal section.
Figure 1B:
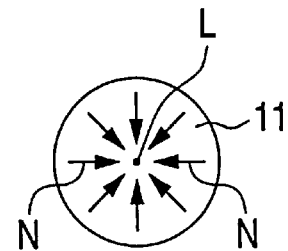
FIG. 1(B) shows a plan view of the orientation conditions.
Figure 2A:
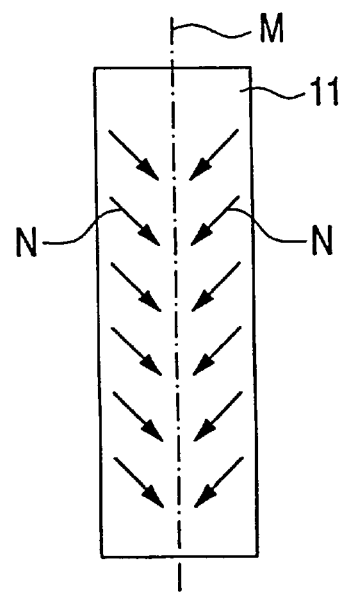
FIG. 2(A) shows orientation conditions of a longitudinal section.
Figure 2B:
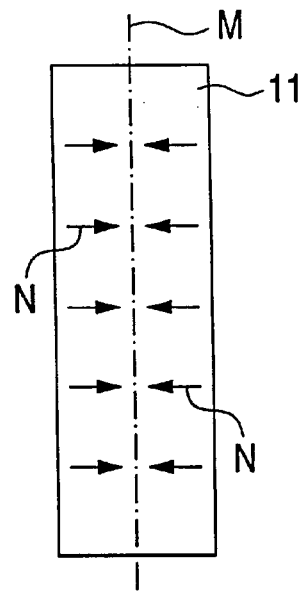
FIG. 2(B) shows a plan view of the orientation conditions.
Figure 3:
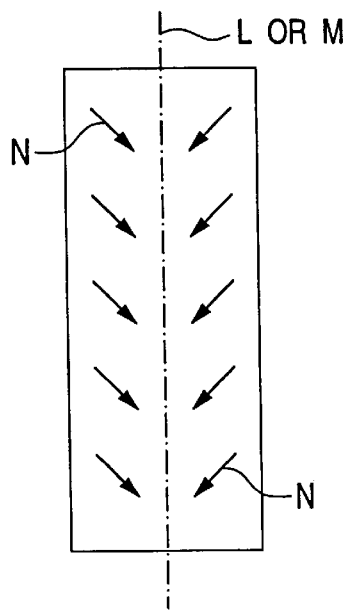
FIG. 3 schematically shows orientation conditions of crystals on a longitudinal section of a molding.
Figure 3:
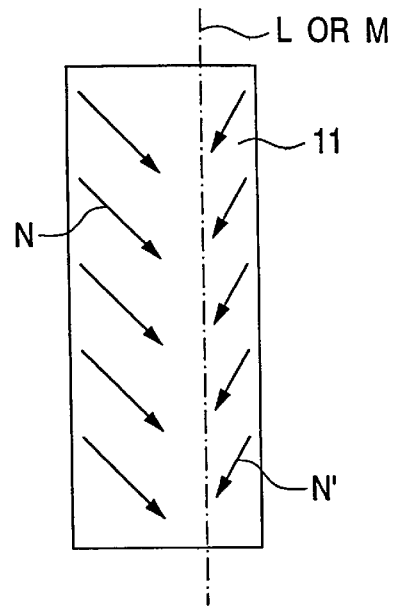
Figure 3:
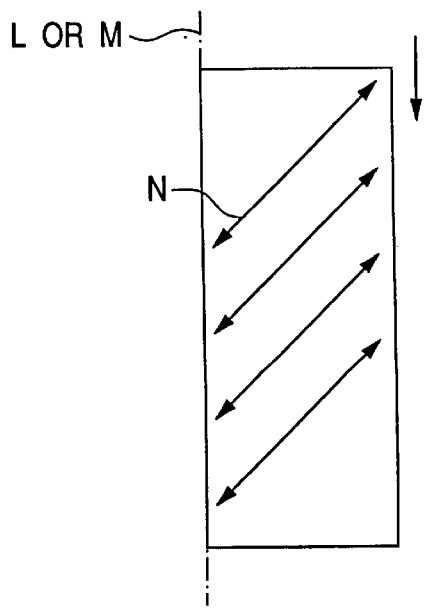
Figure 3:
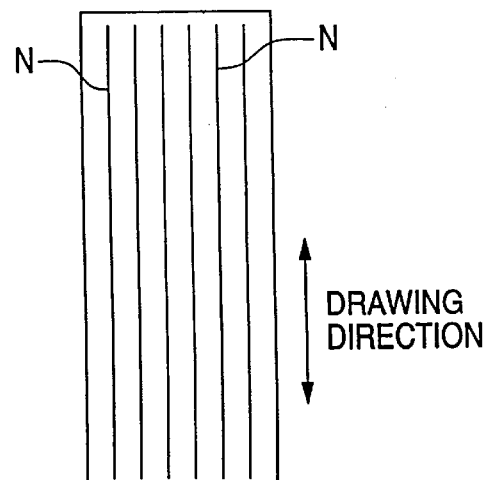

The mark 1 is a billet, 2 is a molding, 2*a* is a container cylinder part, 2*b* is a compression means, 2*c* and 2*d* are cavities, 10 is a compression-oriented molding, 10*a* is a margin material part, 11 is a material for osteosynthesis or an implant material, 11*a* is a conventional implant material, 12 is a white and opaque pin, 20*a* is a diameter-reducing part, 30 is a screw for osteosynthesis, 31 is a screw axis part, 32 is a screw head part and 33 is a rotating jig insertion hole.

Best Mode of Carrying out the Invention

Examples of the present invention are given below by way of illustration and not by way of limitation.

Measuring methods of various physical values are described in the following.

(i) Bending strength and bending modulus: Measured in accordance with the procedure of JIS-K-7203 (1982).

(ii) Tensile strength: Measured in accordance with the procedure of JIS-K-7113 (1981).

(iii) Shear strength: Measured in accordance with the method of R. Suuronen et al. [R. Suuronen, T. Pohjonen et al., J. Mater. Med., (1992) 426].

(iv) Density: Measured in accordance with the procedure of JIS-K-7112 (1980).

(v) Crystallinity: Calculated from the melt peak enthalpy measured using a differential scanning calorimeter (DSC).

(vi) Breakdown torque: A value measured by a torque tester (Neji Tester, manufactured by Sinpo Kogyo).

EXAMPLE 1

Example of Orientation by Compression deformation; case 1

Using an extruder, poly L-lactic acid having a viscosity average molecular weight of 400,000 was melt-extruded at 190° C. to obtain a prismatic billet in a size of height×width=60 mm×60 mm and 50 mm in length having a viscosity average molecular weight of 300,000. This billet was put into a container cylinder part of a forming mold which has the same sectional shape, heated at 110° C. and then press-charged into a cavity of height×width×length=35 mm×35 mm×120 mm with a pressure of 2,000 kg/cm² through its diameter-reducing part. After cooling, the resulting prismatic compression-oriented molding (deformation degree R≈3) was released from the forming mold, its margin material part was cut off and then said molding was sliced in the longitudinal direction into a plate-like shape of 30 mm in thickness, thereby producing a plate for osteosynthesis.

Physical properties of the thus obtained plate for osteosynthesis were compared with those of a comparative example plate for osteosynthesis having the same shape obtained from the polylactic acid by a triple drawing in the longitudinal axis direction, with the results shown in the following Table 1. In this connection, density of the billet was measured before its press charging and shown in Table 1.

on the surface of the diameter-reducing part when the billet was press-charged into the cavity of the forming mold, so that it became qualitatively dense without anisotropy in view of strength.

In addition, since molding temperature and rate for plastic deformation were properly selected, its crystallinity was controlled at a relatively low level. Accordingly, this plate has excellent toughness and its degradation rate is within such a range that it does not induce biological reactions.

EXAMPLE 2

Example of Orientation by Compression Deformation; Case 2

Figure 4:
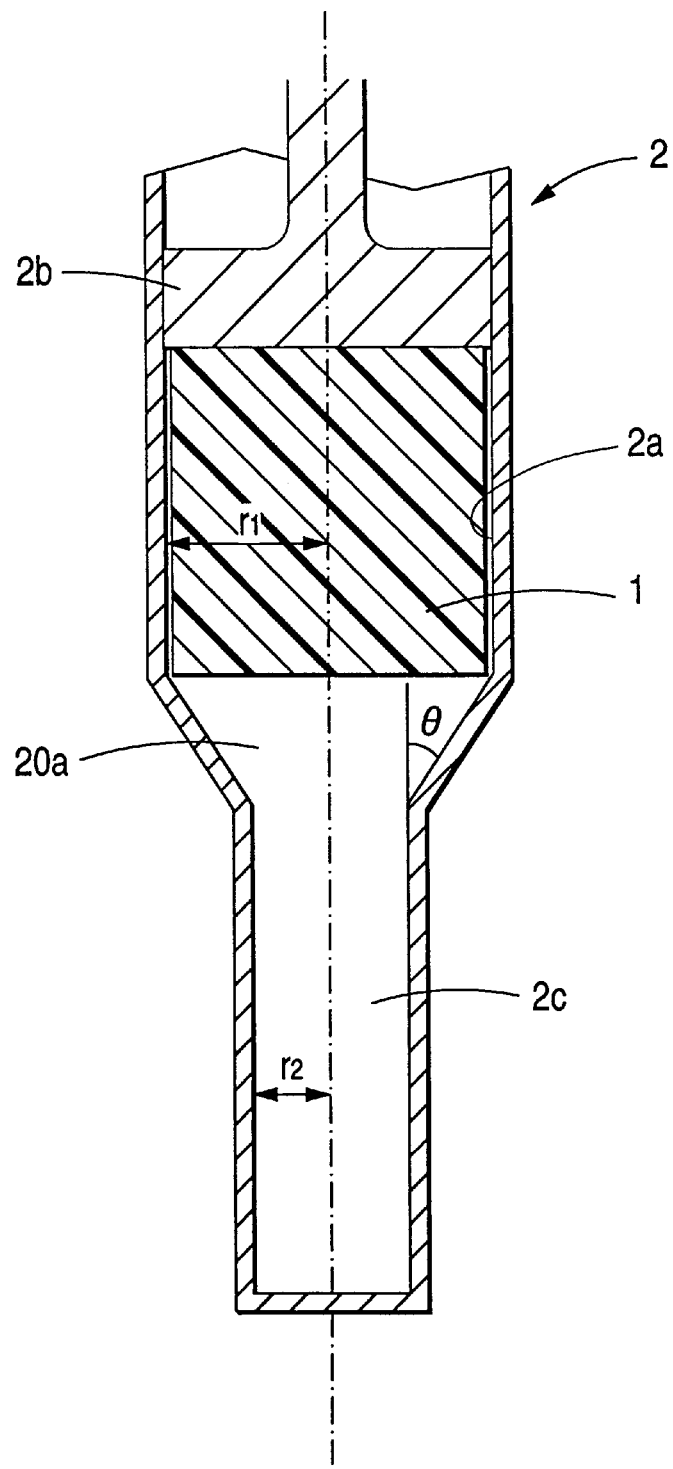
FIG. 4 is a sectional view showing conditions of orientation molding by compression deformation, before press charging of a billet into the cavity of a forming mold.

Using an extruder, poly L-lactic acid having a viscosity average molecular weight of 400,000 was melt-extruded at 190° C. to obtain a cylindrical billet of 13 mm in diameter and 50 mm in length having a viscosity average molecular weight of 300,000. As shown in FIG. 4, this billet was put into a container cylinder part of a forming mold, having a cylindrical shape of 13 mm in diameter, heated at 110° C.

TABLE 1

|  | Molding method | Deformation degree (draw ratio) | Density (g/cm³) | Crystallinity (%) | Bending strength (MPa) | Bending modulus (GPa) | Shear strength (MPa) |
|---|---|---|---|---|---|---|---|
| Example 1 | compression orientation | deformation degree 3.0 | 1.26 | 50.3 | 300 | 6.5 | 96 |
|  | billet | — | 1.24 | — | — | — | — |
| Comparative Example 1 | uni-axially drew orientation | draw ratio 3.0 | 1.24 | 53.3 | 260 | 6.0 | 90 |

In this connection, the drawn plate of the comparative example was obtained by triple-drawing of the same billet in the longitudinal axis direction in a paraffin bath of 110° C.

As shown in Table 1, the plate for osteosynthesis composed of a compression-oriented molding is large in density and has high bending strength, bending modulus and shear strength in comparison with the plate for osteosynthesis composed of a uni-axially drawn article, and the density is higher than that of the billet before its press charging as a matter of course.

That is, it is considered that strengths of the plate for osteosynthesis obtained by the production method of the present invention were increased as a whole in comparison with those of the qualitatively dilute uni-axially oriented article obtained by drawing orientation, because crystals of the former plate were basically oriented along the surface of the diameter-reducing part, diagonally from its peripheral toward the central axis, by receiving shear force by friction and then press-charged into a cylindrical cavity of 8.5 mm in diameter and 92 mm in length with a pressure of 1,800 kg/cm² while effecting plastic deformation, thereby obtaining a cylindrical compression-oriented molding (deformation degree R=2.3) having the same size of the cavity.

Thereafter, the compression-oriented molding was subjected to a cutting work to produce a pin for osteosynthesis having a diameter of 3.2 mm and a length of 40 mm, and its physical properties were examined in the same manner as described in Example 1.

Its breakdown torque was also measured by a torque tester. The results are shown in Table 2.

As a comparative example, a pin for osteosynthesis having the same shape and a draw ratio of 2.3 was produced from the poly L-lactic acid by drawing the same billet in the longitudinal axis direction, and its physical properties were measured and compared. The results are shown in Table 2.

TABLE 2

|  | Molding method | Deformation degree (draw ratio) | Density (g/cm³) | Crystallinity (%) | Bending strength (MPa) | Bending modulus (GPa) | Shear strength (MPa) | Breakdown torque (kg · cm) |
|---|---|---|---|---|---|---|---|---|
| Example 2 | compression orientation | deformation degree 2.3 | 1.25 | 47.0 | 260 | 6.3 | 95 | 6.6 |

TABLE 2-continued

|  | Molding method | Deformation degree (draw ratio) | Density (g/cm³) | Crystallinity (%) | Bending strength (MPa) | Bending modulus (GPa) | Shear strength (MPa) | Breakdown torque (kg · cm) |
|---|---|---|---|---|---|---|---|---|
| Comparative Example 2 | uni-axial draw orientation | draw ratio 2.3 | 1.24 | 50.0 | 220 | 5.2 | 88 | 5.8 |

As shown in Table 2, the pin for osteosynthesis obtained by the production method of the present invention has high bending strength and bending modulus and is also dense with a large density in comparison with the pin for osteosynthesis obtained by drawing. Also, it can be seen that the former has a large breakdown torque value and is therefore stronger against torsion than the latter.

As described in the foregoing, these results seem to support that the former showed a large strength against torsion around its longitudinal axis due to reduced anisotropy in view of strength, because its crystal axes are basically oriented along the surface of the diameter-reducing part, diagonally from the outer peripheral of the pin for osteosynthesis toward its central axis, while crystal axes of the latter are uni-axially oriented only in the longitudinal axis direction.

EXAMPLE 3

Example of Orientation by Compression Deformation; Case 3

Using an extruder, poly L-lactic acid having a viscosity average molecular weight of 300,000 was melt-extruded at 188° C. to obtain a cylindrical billet of 13 mm in diameter and 50 mm in length having a viscosity average molecular weight of 220,000. As shown in FIG. 4, this billet was put into a container cavity of a forming mold, having a cylindrical shape of 13 mm in diameter, heated at 100° C. and then press-charged into a cylindrical molding cavity of 10.6 mm in diameter and 60 mm in length with a pressure of 400 kg/cm², thereby obtaining a cylindrical compression-oriented molding (deformation degree R=1.5) having the same size of the cavity. Thereafter, the molding was subjected to a cutting work to produce a pin for osteosynthesis having a diameter of 3.2 mm and a length of 40 mm, and its physical properties were examined in the same manner as described in Example 1.

The results are shown in Table 3.

EXAMPLE 4

Example of Orientation by Forging Deformation; Case 1

Figure 7:
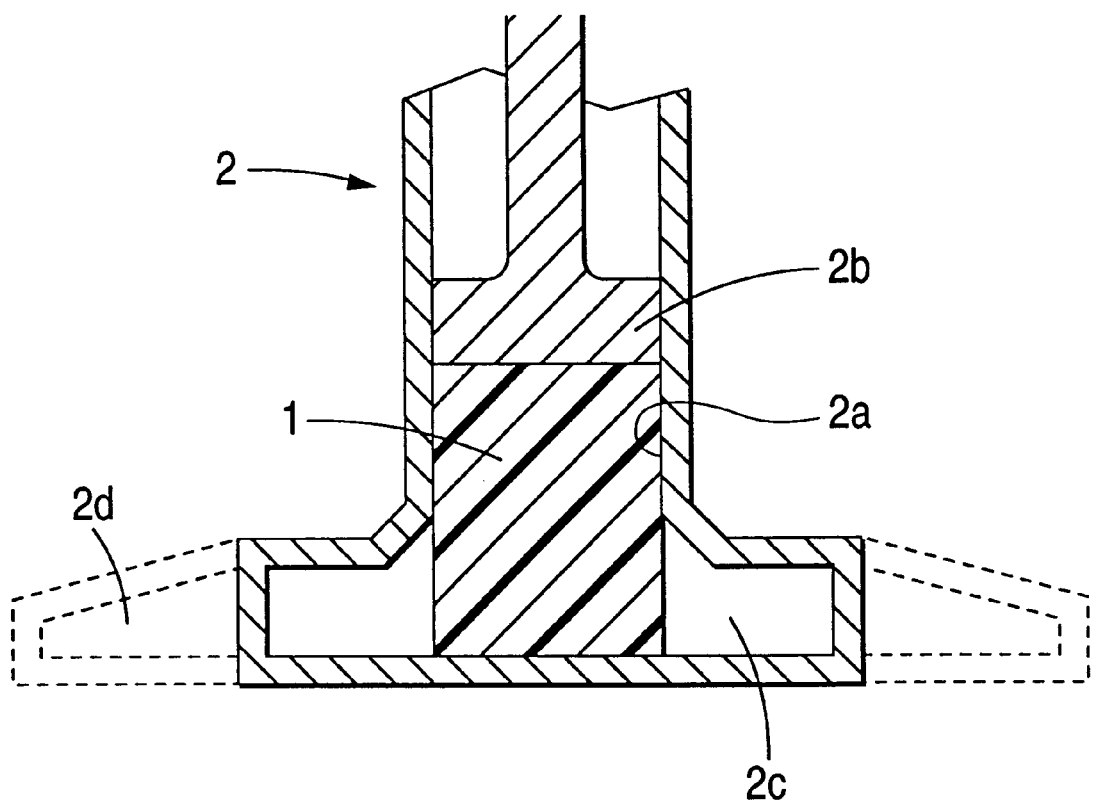
FIG. 7 is a sectional view showing conditions of orientation molding by forging deformation, before press charging of a billet into the cavity of a forming mold.
Figure 8:
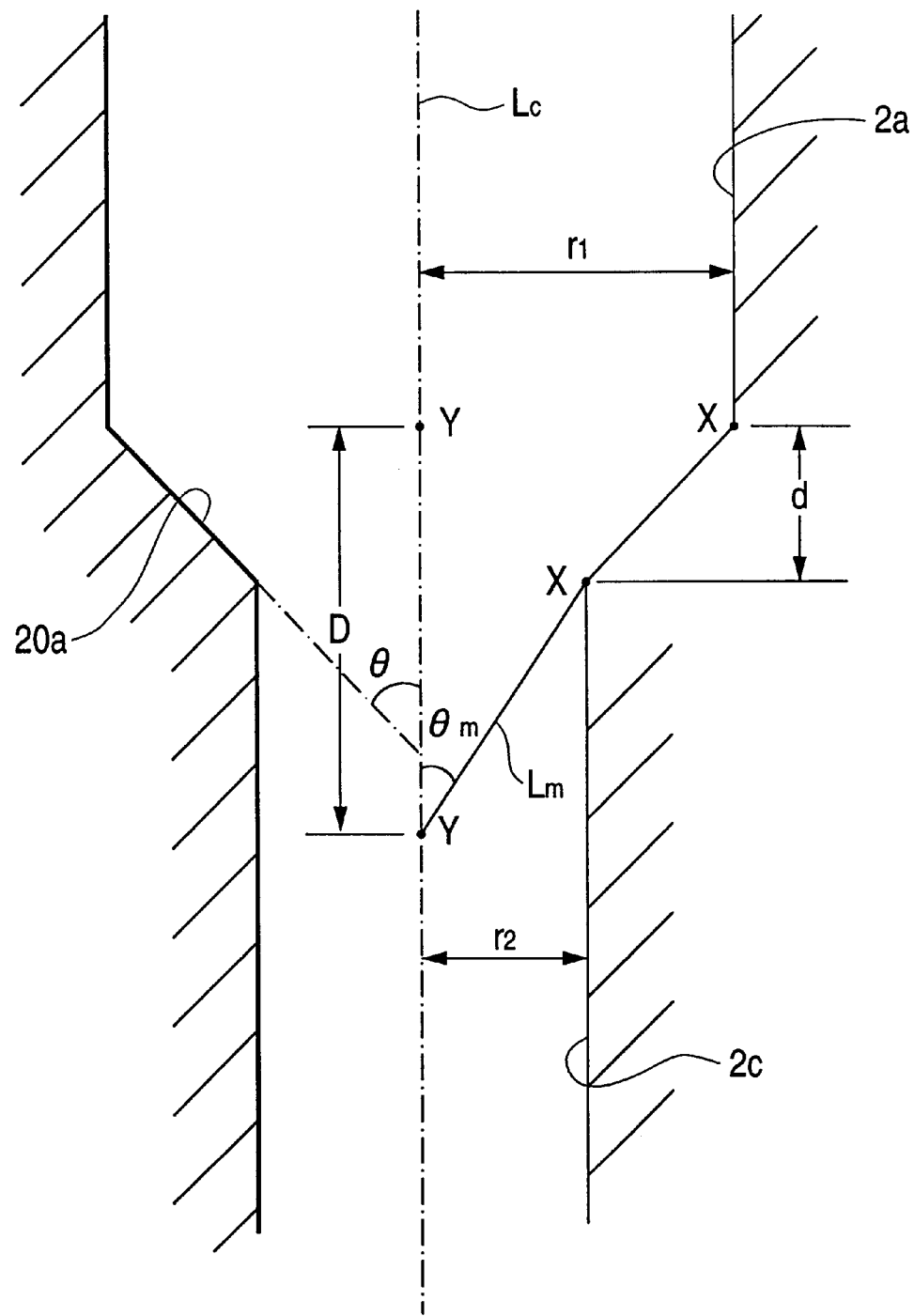
FIG. 8 is a schematic sectional view describing the mechanism of crystal orientation in orientation molding by compression deformation.
Figure 9:
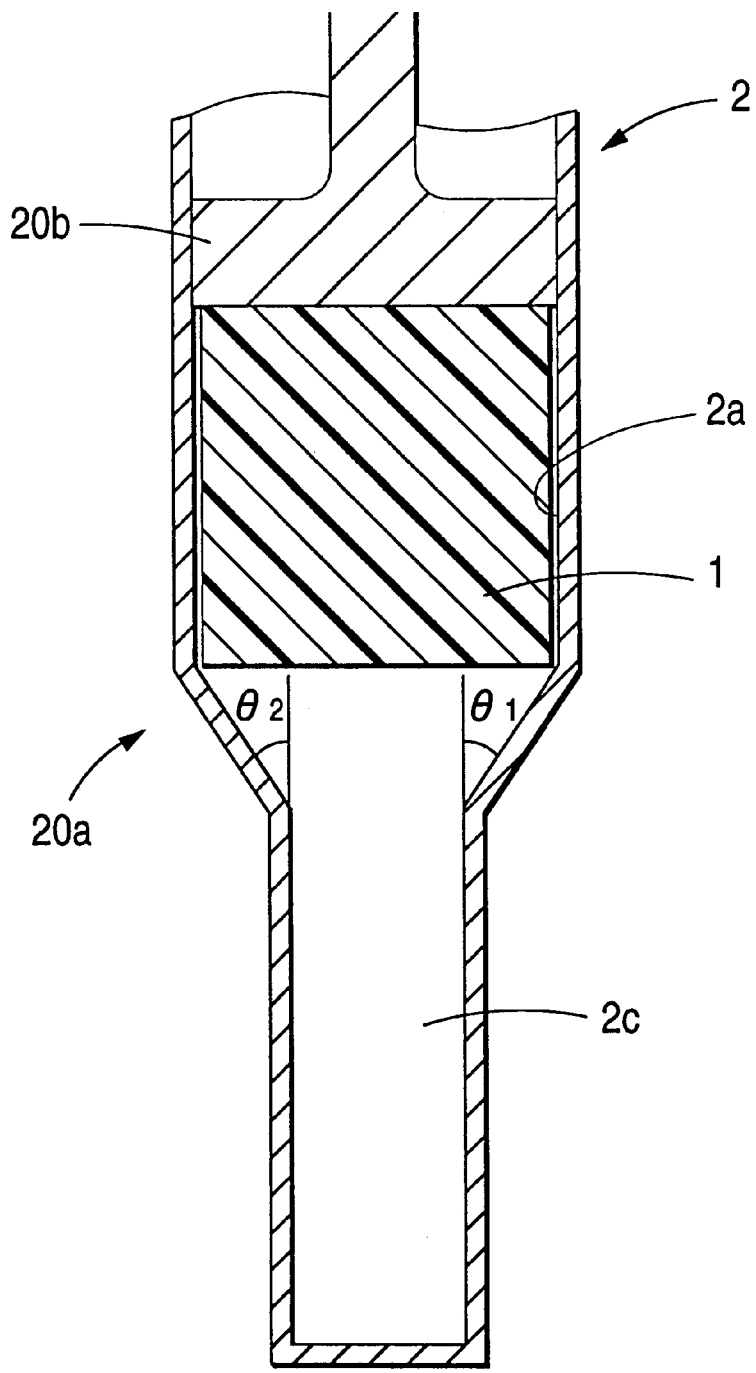
FIG. 9 is a schematic sectional view describing conditions before press charging of a billet into the cavity of a forming mold, in an orientation molding by compression deformation using a forming mold in which both angles of inclination of its diameter-reducing part are different from each other.

Using an extruder, poly L-lactic acid having a viscosity average molecular weight of 250,000 was melt-extruded at 188° C. to obtain a cylindrical billet of 50 mm in diameter and 43 mm in length (including a margin material part) having a viscosity average molecular weight of 200,000. As shown in FIG. 7, using a forming mold having a shape shown in FIG. 4 in which a cylindrical container cylinder part having a diameter of 50 mm is connected to a hollow disc-shaped cavity of 100 mm in diameter and 10 mm in thickness vertically on the same axis, the just described billet was put into the container cylinder part, heated at 100° C. and then press-charged into the cavity with a pressure of 2,500 kg/cm² while effecting plastic deformation, thereby obtaining a disc-shaped forging-oriented molding (deformation degree toward the diameter direction=2.0) having the same size of the cavity.

Thereafter, a test piece was cut out from the forging-molding in the radius direction excluding the central cylindrical part, and its physical properties were measured.

The results are shown in Table 3.

Unlike the crystal face of the aforementioned Example 3, this test piece is a molding having a large face orientation in which multiple orientation axes are radially oriented from the central position of the disc toward its outer peripheral.

EXAMPLE 5

Example of Orientation by Compression Deformation; Case 4

A billet having a viscosity average molecular weight of 300,000 was obtained by extruding polylactic acid having a viscosity average molecular weight of 400,000 under the same conditions of the method of Example 2. Next, this billet was put into a container cylinder part of a forming mold, having a cylindrical shape of 13 mm in diameter and then press-charged into a cylindrical cavity of 11.9 mm in diameter and 46 mm in length with a pressure of 80 kg/cm² under the same conditions of Example 2, thereby obtaining a compression-oriented molding having a deformation degree R of 1.2.

Thereafter, a pin having a diameter of 3.2 mm and a length of 40 mm was produced from this molding by a cutting work, and its physical properties were examined in the same manner as described in Example 1.

The results are shown in Table 3.

TABLE 3

|  | Molding method | Density (g/cm³) | Crystal-linity (%) | Bending strength (MPa) | Bending modulus (GPa) | Shear strength (MPa) | Breakdown torque (kg · cm) |
|---|---|---|---|---|---|---|---|
| Example 3 | compression orientation | 1.25 | 43.3 | 165 | 5.0 | 90 | 5.8 |
| Example 4 | forging orientation | 1.25 | 40.5 | 208 | 6.0 | 93 | — |
| Example 5 | compression orientation | 1.25 | 42.0 | 148 | 5.0 | 88 | 5.5 |
| Example 7 | compression orientation | 1.25 | 35.6 | 210 | 5.1 | 80 | 4.8 |

The bending strength and density were higher than those of a drawn article obtained by a uni-axial drawing at a draw ratio identical to the deformation degree R. However, the compression bending strength of this molding was lower than the lower limit value of from 150 to 200 MPa which is the strength of general cortical bones. In consequence, it seems that a deformation degree R of at least 1.5 or more like the case of Example 2 is necessary to obtain a strength of 150 MPa or more.

EXAMPLE 6

Example of Orientation by Compression Deformation; Case 5

An attempt was made to obtain a compression-oriented molding having a deformation degree R of 6.0 by putting the same polylactic acid billet obtained in Example 5 into a container cylinder part of a forming mold, having a cylindrical shape of 13.0 mm in diameter, and press-charging it into a cavity of 5.3 mm in diameter and 220 mm in length under the same conditions of Example 2. However, an extremely high pressure of 10,000 kg/cm² was required for the press charging. Also, cracks were found in the thus obtained molding.

In the same manner, another attempt was made on the case of a deformation degree R of 5.5. The thus obtained molding had cracks partially and therefore was not sufficiently satisfactory.

However, a compression-oriented molding in good quality was obtained when the angle of inclination of the diameter-reducing part was reduced (150) and the mold was treated in such a manner that its surface became slippery.

EXAMPLE 7

Example of Orientation by Compression Deformation; Case 6

Using a copolymer of poly L-lactic acid and polyglycolic acid (molar ratio=95:5) having a viscosity average molecular weight of 400,000, a cylindrical compression-oriented molding was prepared by the same method of Example 2 and its physical properties were measured. The results are shown in Table 3.

Since the crystallinity of a copolymer is reduced to a lower level than that of a homopolymer, its strength is also reduced to a slightly lower level than that of the homopolymer, but this compression-oriented molding has sufficient strength to be used as a material for osteosynthesis and is possessed of an advantage in that its degradation in the living body is faster than the case of a homopolymer.

Confirmation Test

The following experiments were carried out in order to confirm that the oriented molding obtained by the present invention has an orientation form which is different from a uni-axially oriented molding obtained by drawing in the longitudinal axis direction.

Figure 11A:
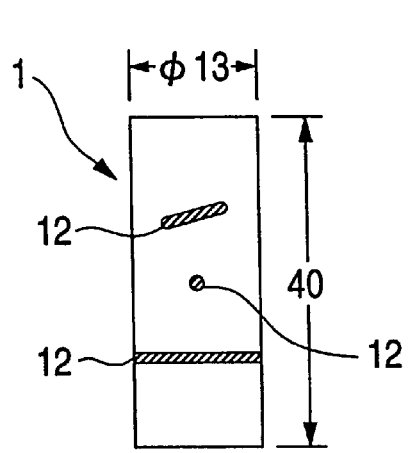
FIG. 11(A) is a side elevation view of a billet used in the Confirmation Test (1)
Figure 11B:
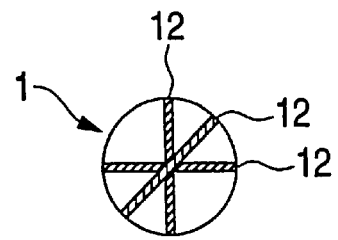
FIG. 11(B) is its plan view.

(1) As shown in FIG. 11, a through hole of 2.0 mm$\phi$ was opened through a transparent poly L-lactic acid billet obtained by the aforementioned melt molding method, and the hole was completely filled by inserting a white and opaque poly L-lactic acid pin 12 having the same diameter which had been obtained by mixing the same poly L-lactic acid with an inorganic white pigment.

Figure 12:
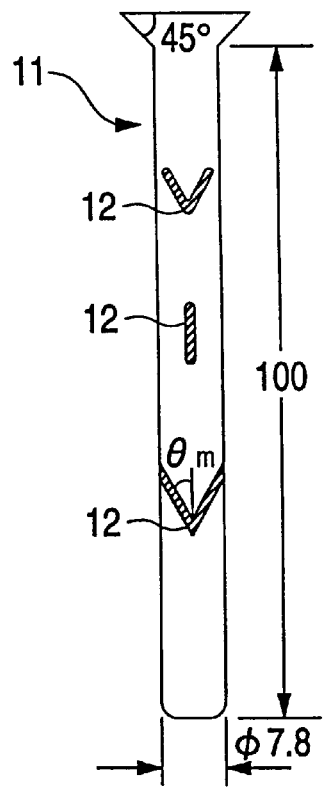
FIG. 12 is a side elevation view of a round bar after orientation molding by compression deformation carried out in the Confirmation Test (1).

This was charged into the mold described in Example and subjected to compression orientation molding by the same method at an angle of inclination of 45° of the diameter-reducing part and at a deformation degree of 2.8. As the results, a pin 12 formed into the shape of FIG. 12 was obtained.

The white and opaque round bar having a small diameter formed a bent condition with an angle of θm=28° bordering its central part. Thickness of the round bar in the formed poly L-lactic acid transparent article was deformed not in the diameter direction but thickly in the longitudinal direction (into a thickness corresponding to the deformation degree).

Figure 13A:
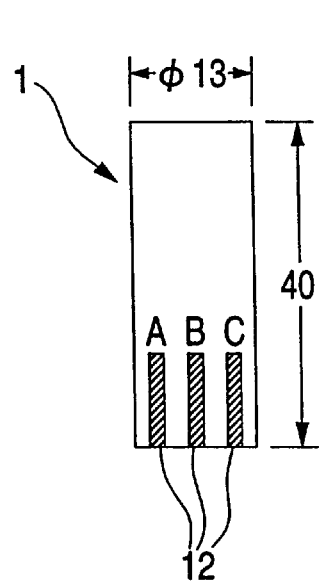
FIG. 13(A) is a side elevation view of a billet used in the Confirmation Test (2)
Figure 13B:
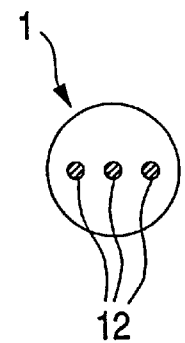
FIG. 13(B) is its plan view.

(2) Similar to the case of (1), three small holes of $\phi$ 2.0×10 mm were opened through the bottom part of the transparent poly L-lactic acid billet as shown in FIG. 13, and the white and opaque poly L-lactic acid pin 12 used in (1) was inserted into each hole.

Figure 14:
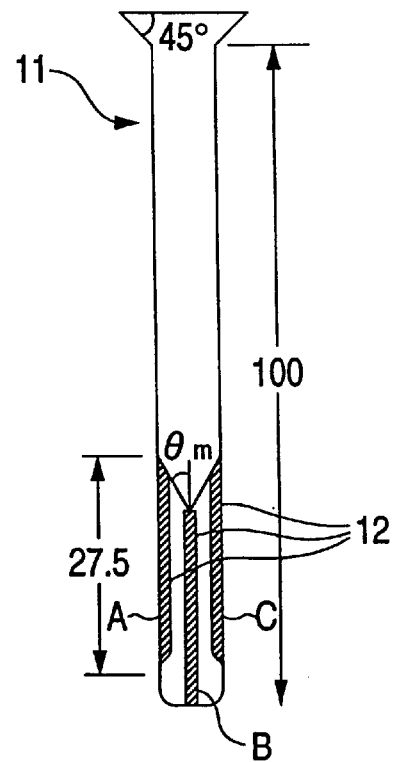
FIG. 14 is a side elevation view of a molding after orientation molding by compression deformation carried out in the Confirmation Test (2).
Figure 15A:
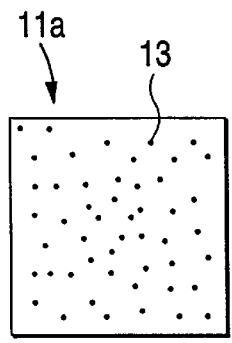
FIG. 15 is a schematic view in which internal structure of the composite material of the present invention is compared with those of the prior art composite materials, with regard to the reinforcing methods of composite materials.
Figure 15B:
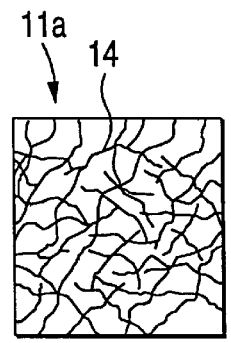
Figure 15C:
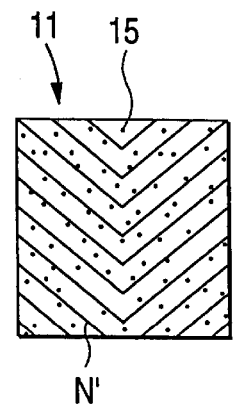

Thereafter, compression orientation molding was carried out at a deformation degree of 2.8. As the results, a molding having a shape shown in FIG. 14 was obtained. The small diameter round bar B inserted into the central part of the billet and the round bars A and C both inserted into parts closer to the outer peripheral on the same diameter formed an angle of θm=28°, and B reached the bottom face, but A and C took a floated state from the bottom face as shown in FIG. 14.

Though it is influenced by the angle of inclination (45° in this case) and deformation degree (2.8 in this case) of the taper part of the forming mold of (1) and (2), the angle of 28° was close to the angle of θm≈30° obtained by a theoretical formula $\tan\theta m = \tan\theta/[A(A^{0.5}-1)]$ (in this case, θ=45° and A=2.8).

As is evident from the experiments of (1) and (2), in a molding obtained by an orientation molding through compression deformation using a mold as shown in FIG. 4, a portion of the material on the same diameter of the billet makes progress in the molding cavity ahead of other portions when it is close to the central position and another portion close to the outer peripheral is forced into the molding cavity behind the former.

Thus, it was confirmed that the angle of central material to outer peripheral material is influenced by the angle of the taper face, but it becomes close to the theoretical angle θm in response to the deformation degree.

In other words, the material on the same diameter forms a "cone-shaped" orientation face like a pit dug by an antlion, in which the orientation axes continuously radiate having an angle of θm, and also forms an orientation mode in which these orientation faces are continued in the longitudinal axis direction.

Figure 10A:
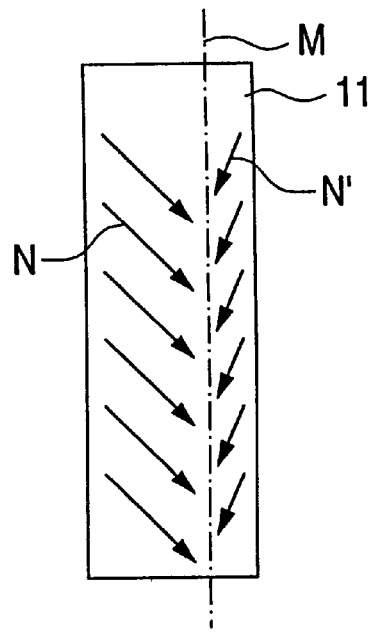
FIG. 10(A) shows orientation conditions of a longitudinal section.
Figure 10B:
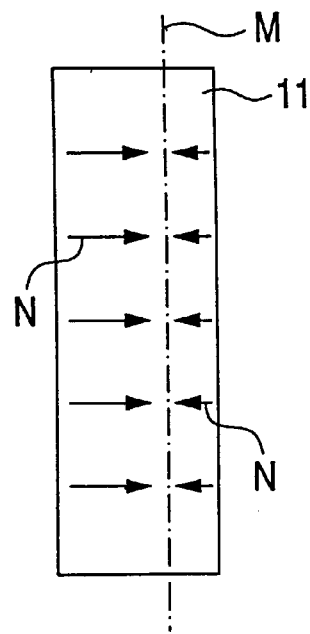
FIG. 10(B) shows a plan view of the orientation conditions.

Such a mode is clearly different from that of the simple uni-axial orientation obtained by drawing in the longitudinal axis direction. It can be easily understood that its application mode is obtained in FIG. 10, and more complex mode of orientation is obtained in the case of the forging molding of FIG. 7.

EXAMPLE 8

Compression Molding; Case 7

Hydroxylapatite (HA) having a maximum particle size of 31.0 μm, a minimum particle size of 0.2 μm and an average particle size of 1.84 μm (sintered at 900° C.) was suspended in ethyl alcohol and added to dichloromethane in which 4% by weight of poly L-lactic acid (PLLA) having a viscosity cavity having a hole of 7.8 mm in diameter and 90 mm in length which was connected to the container cylinder part via a diameter-reducing part, thereby obtaining a compression-oriented molding having the same shape of the cavity, in which PLLA and HA are compounded and HA is uniformly dispersed. In this case, θ=15°.

When sectional area of the thus obtained molding is defined as S, and sectional area of the billet before its plastic deformation is defined as $S_0$, the deformation degree $R=S_0/S=2.8$.

Table 4 shows comparison of physical properties of the thus obtained compression-oriented moldings of composite HA/PLLA (sample Nos. 2, 3, 4, 5 and 6) with those of a PLLA compression-oriented molding which has a deformation degree of 2.8 and is composed of PLLA alone (sample No. 1: Reference Example 1) and a non-oriented molding which contains 30% by weight of HA but is not treated by compression orientation molding (sample No. 3': Reference Example 2).

As shown in Table 4, mechanical physical properties of the compression-oriented moldings of compounded PLLA containing HA are markedly improved.

TABLE 4

| Composition | 1 PLLA HA 0 wt % compression orientation | 2 PLLA HA 20 wt % compression orientation | 3 PLLA HA 30 wt % compression orientation | 3' PLLA HA 30 wt % no orientation | 4 PLLA HA 40 wt % compression orientation | 5 PLLA HA 50 wt % compression orientation | 6 PLLA HA 60 wt % compression orientation | 7 PLLA HA 30 wt % uni-axial drawing |
|---|---|---|---|---|---|---|---|---|
| Bending strength (MPa) | 260 | 273 | 280 | 148 | 284 | 230 | 175 | 145 |
| Bending modulus (GPa) | 6.5 | 7.1 | 7.8 | 4.9 | 9.5 | 12.5 | 14.3 | 3.3 |
| Tensile strength (MPa) | 157 | 168 | 175 | 92 | 172 | 165 | 160 | 65 |
| Shear strength (MPa) | 96 | 104 | 11.3 | 98 | 117 | 120 | 125 | 61 |
| Crystallinity (%) | 49 | 44.2 | 42.5 | 2.3 | 43.6 | 43.8 | 44.0 | 43.5 |
| Density[1] | 1.265 | 1.415 | 1.505 | 1.505 | 1.606 | 1.723 | 1.857 | 0.924 |
| Ratio of PLLA[2] (%) | 100 | 89.5 | 83.3 | 83.3 | 76.2 | 68.1 | 58.7 | — |

Note 1): The density is a theoretical value converted from true specific gravity of bioceramics, the same shall apply hereinafter.
Note 2): Weight of PLLA contained in the same shape of HA-containing compression-oriented molding when weight of a molding of PLLA alone is defined as 100.

average molecular weight of 400,000 had been dissolved, and the mixture was stirred to effect uniform dispersion without causing secondary aggregation of HA. While stirring, to this was further added ethyl alcohol, thereby effecting co-precipitation of PLLA and HA. Next, this was filtered and completely dried to obtain granules of PLLA in which HA having the aforementioned particle size was uniformly dispersed at a ratio of 20, 30, 40, 50 or 60% by weight.

This was subjected to melt molding at 185° C. using an extruder to obtain a cylindrical billet having a diameter of 13.0 mm, a length of 40 mm and a viscosity average molecular weight of 250,000.

Figure 5:
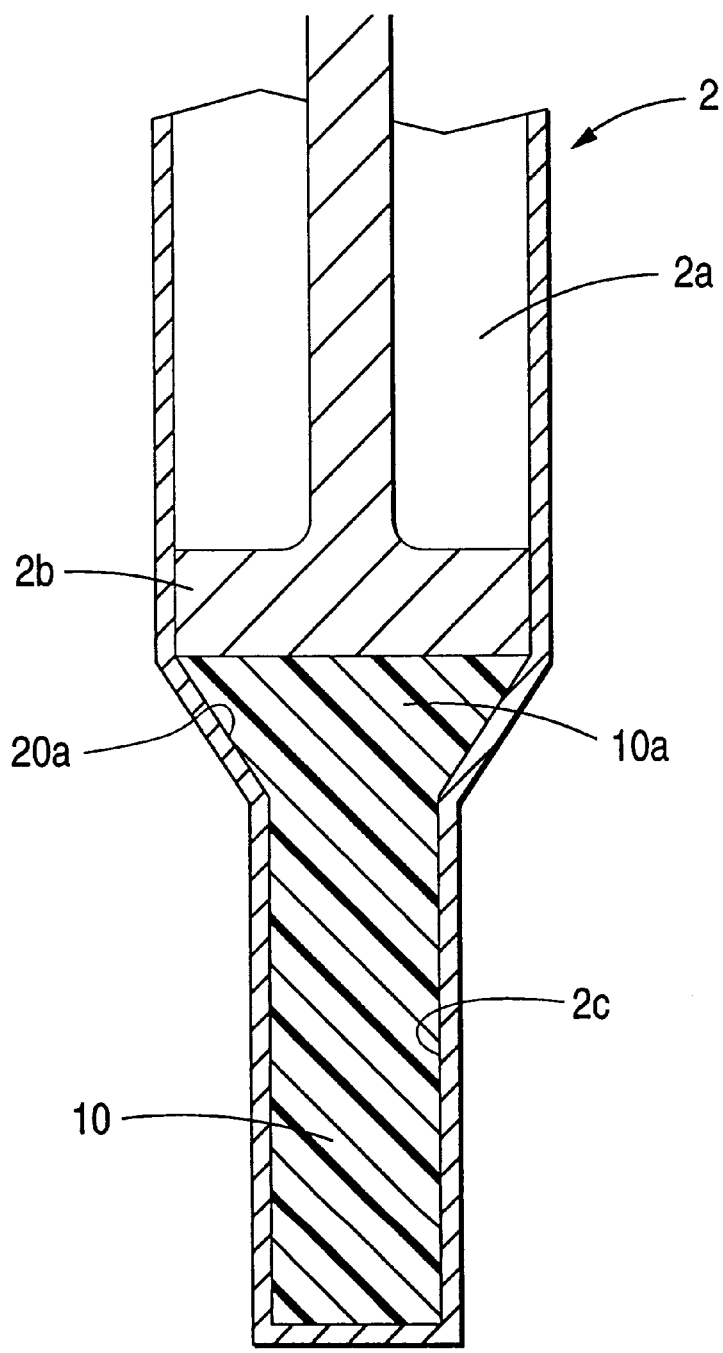
FIG. 5 is a sectional view showing conditions of orientation molding by compression deformation, after press charging of a billet into the cavity of a forming mold.
Figure 6:
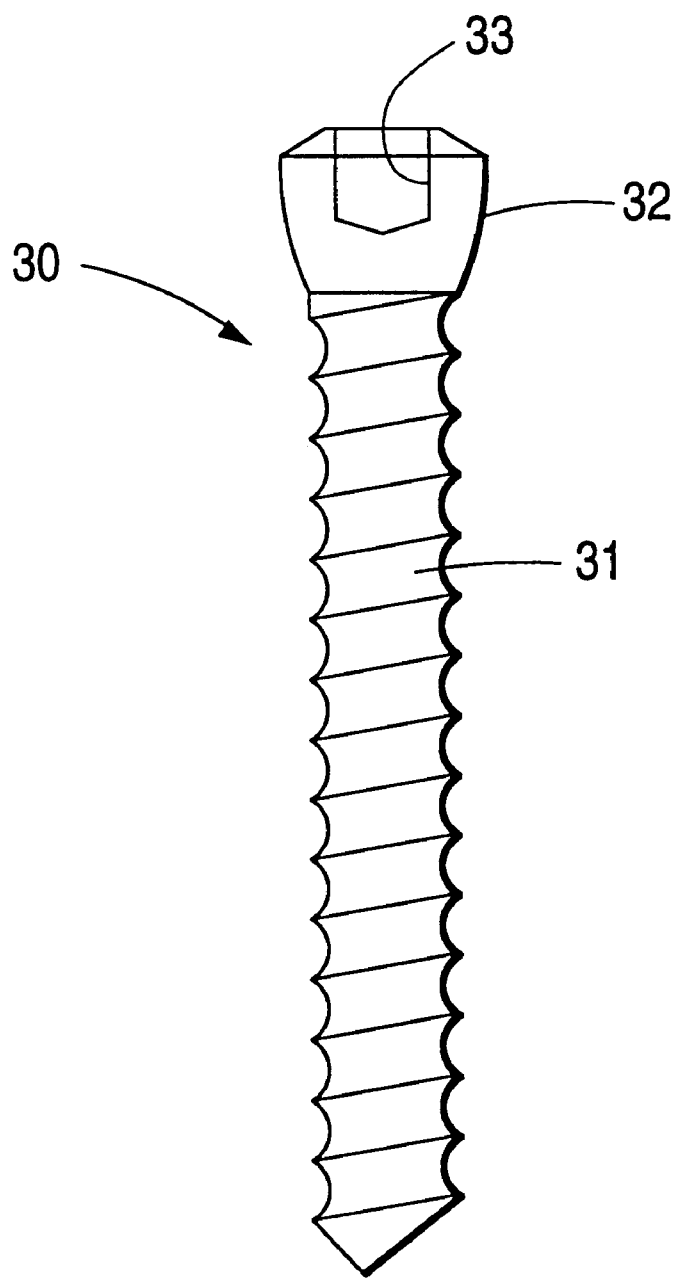
FIG. 6 is an elevation view showing an example of screw for osteosynthesis obtained by finally carrying out a cutting work.

Next, as shown in FIG. 4 and FIG. 5, this billet was heated at 110° C. in a container cylinder part having a hole of 13.0 mm in diameter and then molded by press-charging it into a As another reference example, a drawing-oriented molding (sample No. 7) was prepared by the conventional uni-axial drawing in which the force for orientation is added toward a direction withdrawing from the material, which is the opposite direction of compression orientation of the present invention, and in which the orientation mode is also different, with its physical properties also shown in Table 4. The drawing was carried out after heating in liquid paraffin at 110° C.

Since the filler and polymer of this molding move differently starting from the interface of these materials at the time of deformation by drawing, it was a poor article in which the material surface became fibrous to be torn off and countless large and small voids were formed therein starting at the interface of both materials.

Accordingly, reproducible physical values were not obtained, and the values were low. Among this type of samples, the sample No. 7 shown in Table 4 showed the most better values.

Also, it was a dilute article having a low density of 0.924 because of the formation of countless voids, so that it was considered that penetration of biological fluid from external of the article would occur easily and its degradation would also be fast.

Based on these results, it was confirmed that an implant material having physical properties intended by the present invention cannot be obtained by uni-axial drawing.

In addition, its strength values were so low that it cannot be used as an implant material.

Comparative Example 3

Compression Molding

Using PLLA having a viscosity average molecular weight of 400,000 and HA having a maximum particle size of 100 μm and an average particle size of 60 μm (sintered at 900° C.), PLLA granules in which 30% by weight of HA was uniformly dispersed were obtained by the same method and under the same conditions of Example 8. These granules were subjected to melt extrusion using an extruder in the same manner as described in Example 8 to obtain a cylindrical billet having a diameter of 13.0 mm, a length of 40 mm and a viscosity average molecular weight of 250,000.

Next, this billet was press-charged into the hole of forming mold by the same method and under the same conditions of Example 8, thereby obtaining a compression-oriented molding of composite HA/PLLA of R=2.8 in which HA is uniformly dispersed.

Physical properties of the thus obtained molding were compared with those of the molding of Example 8 containing 30% by weight of HA (sample No. 3), with the results shown in Table 5.

TABLE 5

| Average particle size of HA (μm) | Bending strength (MPa) | Bending modulus (GPa) |
| --- | --- | --- |
| 60 | 250 | 7.0 |
| 1.84 | 280 | 7.8 |

In comparison with the case of Example 8 (sample No. 3) having an average particle size of 1.84 μm, the case of Comparative Example 3 having an average particle size of 60 μm showed lower strengths. In the bending strength test, the case of Comparative Example 3 reached its yielding point and was broken at the time of the maximum loading, but the case of Example 8 (sample No. 3) was not broken.

The reason for this is that, in spite of the high degree orientation of PLLA, large particles of HA or large brittle assembled masses of HA are distributed in a large number, so that the matrix of oriented PLLA is interrupted by HA and its strength therefore cannot be expressed.

On the contrary, the breakage did not occur at the time of the maximum loading in the case of Example 8 (sample No. 3) which contains assembled HA masses of 31.0 μm even as the maximum particle size. In the same manner, the breakage did not occur in the case of a compression-oriented molding of Example 13 which, as will be described later, is a composite material with un-sintered hydroxylapatite particles having a maximum particle size of 45 μm or containing assembled masses thereof.

Since external load is always applied to an implanted material for osteosynthesis, it is possible that a material having insufficient stress against this load will be broken during the period after operation until bone healing. Accordingly, the implant of interest must have toughness in addition to high strength, and a property of not causing breakage at the time of yielding is extremely important for the implant. In consequence, it is necessary that particles or assembled masses of particles have a maximum particle size of approximately 50 μm or less in accomplishing the present invention which also satisfies such a mechanical property.

EXAMPLE 9

Compression Molding; Case 8

Using PLLA having a viscosity average molecular weight of 220,000 and 180,000 and the same HA of Example 8, PLLA granules in which 30% by weight of HA was uniformly dispersed were obtained by the same method and under the same conditions of Example 8 and then extruded using an extruder to obtain a cylindrical billet having a diameter of 13.0 mm, a length of 40 mm and a viscosity average molecular weight of 150,000 and 100,000.

Next, this billet was press-charged into the same forming mold of Example 8, thereby obtaining a compression-oriented molding of composite HA/PLLA of R=2.8 in which HA is uniformly dispersed.

Physical properties of the thus obtained compression-oriented moldings were compared with those of reference example compression-oriented moldings composed of PLLA alone having the same respective molecular weights, with the results shown in Table 6.

TABLE 6

| Samples | Bending strength (MPa) | Bending modulus (GPa) | Crystallinity (%) |
| --- | --- | --- | --- |
| PLLA - HA 30 wt % Mv = 150,000, R = 2.8 | 245 | 7.0 | 44.6 |
| PLLA 100% Mv = 150,000, R = 2.8 | 210 | 5.5 | 50.0 |
| PLLA - HA 30 wt % Mv = 100,000, R = 2.8 | 199[1)] | 7.3 | 46.0 |
| PLLA 100% Mv = 100,000, R = 2.8 | 190 | 4.5 | 52.0 |

(Note 1) Breakage at the yielding point

In comparison with the case of Example 8, the molding obtained from a billet of 150,000 in viscosity average molecular weight has a slightly lower strength, but the bending strength can fully withstand its use as a material for osteosynthesis. Also, its strength and elastic modulus were higher than those of the oriented molding of PLLA alone.

On the contrary, the molding obtained from a billet of 100,000 in viscosity average molecular weight showed increased bending strength in comparison with the case of PLLA alone but was broken at the yielding point.

However, a molding which is not broken at the time of yielding can be obtained depending on conditions when charging amount of the bioceramics particles is 10% by weight. When molecular weight of a polymer is reduced, its specific strength is also reduced in general. It seems that the molding having a viscosity average molecular weight of 100,000 was broken because of reduced toughness as a composite material due to entrapping of a large amount of HA.

In consequence, it is judged that the lower limit of viscosity average molecular weight of the billet is 100,000 necessary for having both sufficient strength (rigidity) and toughness even when HA is entrapped.

EXAMPLE 10

Compression Molding; Case 9

Using PLLA having a viscosity average molecular weight of 400,000 and the same HA of Example 8, PLLA granules in which 15% by weight of HA was uniformly dispersed were obtained by the same method and under the same conditions of Example 8 and then extruded using an extruder to obtain a cylindrical billet having a diameter of 13.0 mm, a length of 40 mm and a viscosity average molecular weight of 250,000.

Next, as shown in FIG. 4, this billet was press-charged into a forming mold in which a container cylinder part having a diameter of 13.0 mm was connected to a cavity having a diameter of 7.0 mm and a length of 113 mm, or a forming mold in which a container cylinder part having a diameter of 14.5 mm was connected to a cavity having a diameter of 11.8 mm and a length of 57 mm, thereby obtaining a compression-oriented molding of composite HA/PLLA of R=3.5 and R=1.5 in which HA is uniformly dispersed. In this case, θ=15°.

Physical properties of the thus obtained moldings were compared with those of reference example compression-oriented moldings composed of PLLA alone having respective values of R=3.5 and R=1.5, with the results shown in Table 7.

TABLE 7

| Samples | Bending strength (MPa) | Bending modulus (GPa) | Crystal-linity (%) |
|---|---|---|---|
| PLLA - HA 15 wt % R = 3.5 | 307 | 8.0 | 50.7 |
| PLLA 100% R = 3.5 | 275 | 7.2 | 54.5 |
| PLLA - HA 15 wt % R = 1.5 | 172 | 6.3 | 40.1 |
| PLLA 100% R = 1.5 | 165 | 4.8 | 44.6 |

As is evident from these results, the molding of R=3.5 has high strength (rigidity) and high toughness, which further exceed bending strength of the compression-oriented molding consisting of PLLA alone and having almost the same high orientation level. Since its crystallinity is lower than that of the molding of PLLA alone, it is a material which exerts low stimulative and inflammatory reactions upon peripheral tissues in the living body. It is considered that such an effect is induced by the action of HA particles to inhibit growth of PLLA crystals and thereby causing their micro-crystallization.

Though bending strength of the molding of R=1.5 is only slightly larger than that of the molding of PLLA alone, this can be used sufficiently as an implant material depending on its application.

EXAMPLE 11

Compression Molding; Case 10

Using PLLA having a viscosity average molecular weight of 400,000 and apatite wollastonite glass ceramics (AW-GC) having an average particle size of 2.7 μm, PLLA granules in which 35% by weight of AW-GC was uniformly dispersed were obtained by the same method and under the same conditions of Example 8 and then subjected to melt extrusion using an extruder to obtain a cylindrical billet having a diameter of 14.5 mm, a length of 45 mm and a viscosity average molecular weight of 220,000.

Next, as shown in FIG. 4, this billet was press-charged into a forming mold in which a container cylinder part having a diameter of 14.5 mm was connected to a cavity having a diameter of 9.6 mm and a length of 83 mm, by the same method and under the same conditions of Example 8, thereby obtaining a compression-oriented molding of composite AW-GC/PLLA of R=2.3 in which AW-GC is uniformly dispersed.

In this case, θ=20°.

Physical properties of the thus obtained compression-oriented molding were compared with those of a reference example PLLA compression-oriented molding of R=2.3 composed of PLLA alone, with the results shown in Table 8.

TABLE 8

| Samples | Bending strength (MPa) | Bending modulus (GPa) | Crystal-linity (%) | Density (g/cm³) |
|---|---|---|---|---|
| PLLA - AW-GC 35 wt % R = 2.3 | 267 | 7.9 | 40.3 | 1.594 |
| PLLA 100% R = 2.3 | 255 | 6.2 | 48.3 | 1.265 |

The thus obtained molding has improved bending strength in comparison with the molding of PLLA alone. When AW-GC is exposed on the surface of this material by its cutting work, AW-GC causes bone induction and actively forms HA layer on the surface after several weeks, so that this can be used as an implant which is markedly effective for bone connection, bone union and bone substitution.

EXAMPLE 12

Compression Molding; Case 11

Using PLLA having a viscosity average molecular weight of 400,000 and alpha type tricalcium phosphate (α-TCP) having a maximum particle size of 22.0 μm and an average particle size of 7.7 μm, PLLA granules in which 25% by weight of α-TCP was uniformly dispersed were obtained by the same method and under the same conditions of Example 8 and then subjected to melt extrusion using an extruder to obtain a cylindrical billet having a diameter of 13.0 mm, a length of 40 mm and a viscosity average molecular weight of 250,000.

Next, as shown in FIG. 4, this billet was press-charged into a forming mold in which a container cylinder part having a diameter of 13.0 mm was connected to a cavity having a diameter of 7.5 mm and a length of 96 mm, by the same method and under the same conditions of Example 8, thereby obtaining a compression-oriented molding of composite α-TCP/PLLA of R=3.0 in which α-TCP is uniformly dispersed. In this case, θ=15°.

Physical properties of the thus obtained compression-oriented molding were compared with those of a reference example molding of R=3.0 composed of PLLA alone, with the results shown in Table 9.

TABLE 9

| Samples | Bending strength (MPa) | Bending modulus (GPa) | Crystal-linity (%) | Density (g/cm³) |
|---|---|---|---|---|
| PLLA - α-TCP 25 wt % R = 3.0 | 287 | 8.4 | 46.5 | 1.471 |
| PLLA 100% R = 3.0 | 265 | 6.9 | 51.3 | 1.265 |

The thus obtained molding has high strength similar to the case of HA-compounded molding and the like, and its bending strength and elastic modulus are higher than those of the molding of PLLA alone. Since α-TCP has higher bioactivity than that of sintered HA, this can be used as a high strength implant effective for bone substitution.

EXAMPLE 13

Compression Molding; Case 12

Using PLLA having a viscosity average molecular weight of 360,000 and un-sintered hydroxylapatite (V-HA), having a maximum particle size of 45 μm and an average particle size of 3.39 μm, PLLA granules in which 40% by weight of HA was uniformly dispersed were obtained by the same method and under the same conditions of Example 8 and then subjected to melt extrusion using an extruder to obtain a cylindrical billet having a diameter of 10.0 mm, a length of 40 mm and a viscosity average molecular weight of 200,000.

Activity Measurement

In order to examine if the activity is high or not, billets were prepared from the PLLA used in Example 13 respectively containing 40% by weight of sintered HA and un-sintered HA, and a small test piece (10×10×2 mm) was prepared from each of the billets and soaked in a pseudo body fluid to observe the amount of calcium phosphate component precipitated on its surface.

As the results, a large amount of crystals started to precipitate on the un-sintered HA/PLLA on the third day and the crystal layer covered entire surface on the sixth day, but the crystal layer did not cover entire surface of the sintered HA/PLLA even on the sixth day.

It is generally known that sintered HA powder does not disappear by its absorption by bone cells, and, in some cases, the cells emit the powder after phagocytosis, and a possibility has been pointed out that the powder has a danger of inducing tissue reactions.

However, un-sintered HA does not have such problems, because it has a completely absorbable property, namely it disappears by its absorption in the living body, and is chemically identical to the HA distributed in the living body. Since a high strength implant of un-sintered HA/PLLA has not been developed yet, the instant example is the basis of the novelty, significance and patentability of the present invention.

Next, as shown in FIG. 4, this billet was press-charged into a forming mold in which a container cylinder part having a diameter of 10.0 mm was connected to a cavity having a diameter of 7.0 mm and a length of 76 mm, by the same method and under the same conditions of Example 8, thereby obtaining a compression-oriented molding of R=2.0 in which un-sintered HA is uniformly dispersed. In this case, θ=30°.

Physical properties of the thus obtained compression-oriented molding were compared with those of a reference example molding of R=2.0 composed of PLLA alone, with the results shown in Table 10.

TABLE 10

| Samples | Bending strength (MPa) | Bending modulus (GPa) | Crystal-linity (%) | Density (g/cm³) |
|---|---|---|---|---|
| PLLA - U-HA 40 wt % R = 2.0 | 250 | 8.0 | 40.3 | 1.606 |
| PLLA 100% R = 2.0 | 210 | 5.5 | 46.7 | 1.265 |

Similar to the case of the compression-oriented molding of sintered HA composite of Example 8, bending strength of the compression-oriented molding of un-sintered HA/PLLA composite was higher than the strength of the molding composed of PLLA alone. Since bioactivity of un-sintered HA is considerably higher than that of sintered HA, a compounded high strength implant material having high bioactivity was obtained.

Being not sintered, the un-sintered HA itself is an inorganic chemical substance and not a powder having high strength such as ceramics, but is a substance more similar to the biological hydroxylapatite in the living body because of no chemical modification by sintering.

Since the matrix polymer was reinforced in the present invention, un-sintered HA was able to be made into a composite material having similar strength to that of sintered HA.

EXAMPLE 14

Compression Molding; Case 13

Using PLLA having a viscosity average molecular weight of 400,000 and beta-type tricalcium phosphate (β-TCP) having a maximum particle size of 45 μm and an average particle size of 2.91 μm, PLLA granules in which 30% by weight of β-TCP was uniformly dispersed were obtained by the same method and under the same conditions of Example 8 and then subjected to melt extrusion using an extruder to obtain a cylindrical billet having a diameter of 13.0 mm, a length of 40 mm and a viscosity average molecular weight of 250,000.

Next, as shown in FIG. 4, this billet was press-charged into a forming mold in which a container cylinder part having a diameter of 13.0 mm was connected to a cavity having a diameter of 8.6 mm, a length of 74 mm, and a diameter of 7.8 mm, a length of 90 mm, by the same method and under the same conditions of Example 8, thereby obtaining a compression-oriented molding of composite β-TCP/PLLA having an R value of 2.3 and 2.8 in which β-TCP is uniformly dispersed. In this case, θ=15°.

Physical properties of the thus obtained compression-oriented moldings were compared with those of the compression-oriented molding of Example 8 obtained from compounded HA/PLLA of R=2.8 in which 30% by weight of HA (sintered at 900° C.) was dispersed, with the results shown in Table 11.

TABLE 11

| Samples | Bending strength (MPa) | Bending modulus (GPa) | Crystallinity (%) | Density (g/cm³) |
|---|---|---|---|---|
| PLLA - β-TCP 30 wt % R = 2.3 | 260 | 7.4 | 40.7 | 1.536 |
| PLLA - β-TCP 30 wt % R = 2.8 | 276 | 7.7 | 42.3 | 1.536 |
| PLLA - HA 30 wt % R = 2.8 | 280 | 7.8 | 42.5 | 1.505 |

The thus obtained moldings have higher bending strength values than those of the moldings of PLLA alone shown in Table 8 and Table 4 respectively having the R values of 2.3 and 2.8. Also, since the molding of R=2.8 has similar level of bending strength to that of the compression-oriented molding of the same R value, it was revealed that a high strength compression-oriented molding can be obtained also by compounding β-TCP.

EXAMPLE 15

Compression Molding; Case 14

Using PLLA having a viscosity average molecular weight of 400,000 and tetracalcium phosphate (TeCP) having a maximum particle size of 30.0 μm and an average particle size of 10.0 μm, PLLA granules in which 15% by weight and 25% by weight of TeCP was uniformly dispersed were obtained by the same method and under the same conditions of Example 8 and then melted using a compression molding machine to obtain a cylindrical billet having a diameter of 13.0 mm, a length of 40 mm and a viscosity average molecular weight of 250,000.

Next, as shown in FIG. 4, the billet containing 15% by weight of TeCP was press-charged into the forming mold of Example 10, and the billet containing 25% by weight of TeCP into the forming mold of Example 12, by the same method and under the same conditions of Example 8, thereby obtaining compression-oriented moldings of TeCP/PLLA having respective R values of 3.5 and 3.0 in which TeCP is uniformly dispersed. In this case, θ=15°.

Physical properties of the thus obtained TeCP/PLLA composite compression-oriented moldings were compared with those of the compression-oriented molding of Example 10 obtained from compounded HA/PLLA of R=3.5 in which 15% by weight of HA (sintered at 900° C.) was dispersed and the compression-oriented molding of Example 12 of R=3.0 in which 25% by weight of α-TCP was dispersed, with the results shown in Table 12.

TABLE 12

| Samples | Bending strength (MPa) | Bending modulus (GPa) | Crystallinity (%) |
|---|---|---|---|
| PLLA - TeCP 15 wt % R = 3.5 | 300 | 8.0 | 51.3 |
| PLLA - HA 15 wt % R = 3.5 | 307 | 8.5 | 50.7 |
| PLLA - TeCP 25 wt % R = 3.0 | 291 | 8.2 | 47.7 |
| PLLA - α-TCP 25 wt % R = 3.0 | 287 | 8.4 | 46.5 |

The thus obtained moldings are different from those of Examples 10 and 12 in terms of the type of bioceramics contained therein, but their percentage content and R are the same. However, each molding showed almost the same degree of strength. When R is 3.5, markedly high bending strength of exceeding 300 MPa was obtained.

EXAMPLE 16

Compression Molding; Case 15

Using PLLA having a viscosity average molecular weight of 600,000 and anhydrous calcium secondary phosphate (anhydrous calcium hydrogenphosphate: DCPA) having a maximum particle size of 40.0 μm and an average particle size of 5.60 μm, PLLA granules in which 45% by weight of DCPA was uniformly dispersed were obtained by the same method and under the same conditions of Example 8 and then melted using a compression molding machine to obtain a cylindrical billet having a diameter of 8.0 mm, a length of 40 mm and a viscosity average molecular weight of 460,000.

Next, as shown in FIG. 4, this billet was press-charged into a forming mold in which a container cylinder part having a diameter of 8.0 mm was connected to a cavity having a diameter of 5.7 mm and a length of 76 mm, by the same method and under the same conditions of Example 8, thereby obtaining a compression-oriented molding of composite DCPA/PLLA of R=2.0 in which DCPA is uniformly dispersed. In this case, θ=45°.

Physical properties of the thus obtained compression-oriented molding are shown in Table 13.

TABLE 13

| Samples | Bending strength (MPa) | Bending modulus (GPa) | Crystallinity (%) | Density (g/cm³) |
|---|---|---|---|---|
| PLLA - DCPA 45 wt % R = 2.0 | 251 | 9.1 | 40.0 | 1.679 |

Though viscosity average molecular weight of this molding was high, its plastic deformation by press charging was possible, and this was a molding having high bending strength and elastic modulus and also having high strength and toughness.

EXAMPLE 17

Compression Molding; Case 16

Using PLLA having a viscosity average molecular weight of 400,000 and octacalcium phosphate (OCP) having a maximum particle size of 22.0 μm and an average particle size of 8.35 μm, PLLA granules in which 10% by weight and 20% by weight of OCP was uniformly dispersed were obtained by the same method and under the same conditions of Example 8 and then melted using a compression molding machine to obtain a cylindrical billet having a diameter of 13.0 mm, a length of 40 mm and a viscosity average molecular weight of 250,000.

Next, the billet containing 10% by weight of OCP was press-charged into a forming mold in which a container cylinder part having a diameter of 13.0 mm was connected to a cavity having a diameter of 6.1 mm, and the billet containing 20% by weight of OCP into a forming mold in which a container cylinder part having a diameter of 13.0 mm was connected to a cavity having a diameter of 6.5 mm, respectively by the same method and under the same conditions of Example 8, thereby obtaining compression-oriented moldings of OCP/PLLA having respective R values of 4.5 and 4.0 in which OCP is uniformly dispersed. In this case, θ=15°.

Physical properties of the thus obtained compression-oriented moldings are shown in Table 14.

TABLE 14

| Samples | Bending strength (MPa) | Bending modulus (GPa) | Crystallinity (%) |
| --- | --- | --- | --- |
| PLLA - OCP 10 wt % R = 4.5 | 300 | 7.7 | 55.6 |
| PLLA - OCP 20 wt % R = 4.0 | 310 | 8.1 | 52.0 |

Both moldings were high strength moldings having a bending strength of 300 MPa or more. The molding containing 20% by weight of OCP had a lower R value than the molding containing 10% by weight of OCP, but its strength and elastic modulus were higher than the latter case. However, being large in R, it required a pressure of about 10,000 kg/cm² at the time of press charging.

As a reference example, a billet containing 10% by weight of OCP, which can be press-charged relatively easily, was press-charged into a forming mold that can yield R=5.5. However, it required a pressure of higher than 10,000 kg/cm² at the time of its press charging, and generation of a large number of cracks was found in the thus obtained molding. On the basis of these results, it can be said that a deformation degree R of 5 or less is desirable for the compression orientation of PLLA containing bioceramics.

EXAMPLE 18

Compression Molding; Case 17

Using a lactic acid-glycolic acid copolymer [P(LA-GA)] (molar ratio, 90:10) having a viscosity average molecular weight of 380,000 and HA (sintered at 900° C.) having a maximum particle size of 31.0 μm and an average particle size of 1.84 μm, a compression-oriented molding of composite HA/P(LA-GA) of R=2.8 in which 30% by weight of HA is uniformly dispersed was obtained by the same method and under the same conditions of Example 8. In this case, θ=15°.

Physical properties of the thus obtained molding were compared with those of a compression-oriented molding composed of P(LA-GA) alone used as a comparative example, with the results shown in Table 15.

TABLE 15

| Samples | Bending strength (MPa) | Bending modulus (GPa) | Crystallinity (%) |
| --- | --- | --- | --- |
| P(LA-GA) - HA 30 wt % R = 2.8 | 235 | 6.5 | 35.2 |
| P(LA-GA) 100 wt % R = 2.8 | 200 | 5.0 | 39.5 |

Strength of the thus obtained molding was slightly lower than that of the case of PLLA alone shown in Example 8. However, it is fully useful as an implant material.

EXAMPLE 19

Forging Molding

Hydroxylapatite (HA) having a maximum particle size of 31.0 μm, a minimum particle size of 0.2 μm and an average particle size of 1.84 μm (sintered at 900° C.) was suspended in ethyl alcohol and added to dichloromethane in which 4% by weight of poly L-lactic acid (PLLA) having a viscosity average molecular weight of 400,000 had been dissolved, and the mixture was stirred to effect uniform dispersion without causing secondary aggregation of HA. While stirring, to this was further added ethyl alcohol, thereby effecting co-precipitation of PLLA and HA. Next, this was filtered and completely dried to obtain granules of PLLA in which HA having the aforementioned particle size was uniformly dispersed at a ratio of 30 and 40% by weight.

This was subjected to melt molding at 185° C. using an extruder to obtain a cylindrical billet having a diameter of 13.0 mm, a length of 40 mm and a viscosity average molecular weight of 250,000.

Next, as shown in FIG. 7, this billet was put into a container cylinder part of a disc-shaped forming mold having a diameter of 100 mm and a thickness of 10 mm, equipped with a cylinder of 50 mm in diameter projected from the central part of the disc, heated at 100° C. and then subjected to forging molding by intermittently applying a pressure of 3,000 kg/cm², thereby obtaining an HA/PLLA composite molding effected by forging pressurization orientation having the same shape of the disc-shaped part of the forming mold.

A test piece was cut out from the thus obtained molding in the radius direction excluding the cylinder part to measure its physical properties. As the results, it showed a bending strength of 220 MPa, a bending modulus of 7.4 GPa, a density of 1.505 g/cm³ and a crystallinity of 43.0%.

Unlike the case of the aforementioned examples, this molding obtained by forging orientation seems to be an oriented article having different crystal plane in which multiple orientation axes are oriented from the central part of the disc toward its peripheral directions.

EXAMPLE 20

Example of Cutting Work; Surface Observation and Periodical Changes

Each of the HA/PLLA composite compression-oriented moldings obtained in Example 8 was processed into a screw of 4.5 mm in outer diameter, 3.2 mm in root diameter and 50 mm in length, and a pin of 3.2 mm in diameter and 40 mm in length, by cutting the molding with a lathe.

Also, a billet extruded in a plate shape using an extruder was obtained from the PLLA granules of Example 8 in which 30% by weight of HA was dispersed, and then, by the same method and the same conditions of Example 8, the billet was press-charged into a forming mold prepared by connecting a sectionally rectangular (plate-shaped) container cylinder part to a sectionally rectangular cavity having a smaller sectional area than the former, thereby obtaining a plate-shaped molding of R=2.8. The surface of this molding was treated by a cutting work using a slicer to obtain a plate of 2.0 mm in thickness, 20 mm in length and 5 mm in width.

The surface of these screw, pin and plate was observed by a scanning electron microscope. In each of these cutting-processed products, fine particles of HA were exposed on the surface in a uniformly dispersed state without forming large assembled masses by secondary aggregation. Also, their uniform dispersion was found inside of each product. In addition, much larger quantity of HA was exposed on the surface as the content of HA increased.

It was confirmed also that these implants were dense with no voids and that the bioceramics and polymer were close to each other physically excellently. These facts show the ground that the material of the present invention has high mechanical strength, binds to biological bones by their direct contact with the bioceramics and performs bone induction and bone conduction or bone substitution efficiently by maintaining the strength during a period necessary for bone union.

It was confirmed also that the pressure-oriented molding of high strength polymer-bioceramics composite material obtained in the example can maintain its strength at a level almost equal to or higher than that of human cortical bones for 2 to 4 months (6 months or more in some cases) in a pseudo body fluid at 37° C. In addition, it was confirmed by an in vivo test that the material after bone union is degraded, absorbed and bone-substituted faster than the case of the polymer alone, though the degradation behavior varies depending on the composition and structure of the material.

Industrial Applicability

As described in the foregoing, the material for osteosynthesis and composited high strength implant material of the present invention are ideal biomaterials, because they have mechanical strength which is similar to or higher than that of cortical bones and are initially resistant against breakage due to their rigidity and toughness. In the case of the implant material, it maintains its strength during a period until healing of hard tissues through its efficient substitution by biological bones, due to the effect of the bioceramics to bind to biological bones and accelerate bone conduction and bone induction and the biodegradable and bioabsorbable properties of the material, it is degraded and absorbed thereafter at such a gradual rate that it does not generate toxicity upon peripheral bones and the space remained after its disappearance is quickly reconstructed by the living body, in addition to an advantage in that its conditions after operation can be observed by simple X-ray photographing.

Also, the production method of the present invention can be carried out without employing special equipment and severe conditions, so that it has markedly high practical value.

We claim:

1. A material for osteosynthesis having high bending strength and high density which comprises a molding comprising a biodegradable and bioabsorbable crystalline thermoplastic polymer material as a main component, wherein the molecular chains or crystals of said molding are oriented not in a uni-axial direction but in parallel with a plurality of reference axes slanted toward an axis which becomes a mechanical core of said molding occurring along the press-charging direction in the forming mold and/or continued faces of said axis.

2. The material for osteosynthesis having high bending strength and high density according to claim 1, which is a molding in which the polymer material is a polylactic acid or a lactic acid-glycolic acid copolymer.

3. The material for osteosynthesis having high bending strength and high density according to claim 1, which is a pressure-oriented molding in which a part of the polylactic acid or lactic acid-glycolic acid copolymer is crystallized.

4. The material for osteosynthesis having high bending strength and high density according to claim 1, wherein said molding is substantially in a columnar shape, and molecular chains or crystals are oriented along reference axes slanted from its peripheral side toward a central or off-central axis.

5. The material for osteosynthesis having high bending strength and high density according to claim 1, wherein said molding is substantially in a plate shape, and molecular chains or crystals are oriented along reference axes slanted from a peripheral side toward a face of an axis which becomes a mechanical core of said molding, which face is parallel to both sides of the molding and includes axes located at the same distance or different distances from both sides of the molding.

6. The material for osteosynthesis having high bending strength and high density according to any one of claims 1 to 3, wherein the said molding has a crystallinity of from 30 to 60%.

7. The material for osteosynthesis having high bending strength and high density according to any one of claims 1 to 3, wherein crystals of the said molding have crystal faces that are face-oriented along reference axes.

8. The material for osteosynthesis having high bending strength and high density according to any one of claims 1 to 3, wherein the said molding is an oriented article obtained by a compression molding or a forging molding into a closed mold.

9. The material for osteosynthesis having high bending strength and high density according to any one of claims 1 to 3, wherein the said molding is a molding of a polylactic acid or a lactic acid-glycolic acid copolymer having a bending strength of from 160 to 300 MPa and a bending modulus of from 5 to 10 GPa.

10. A method for producing a material for osteosynthesis, which comprises producing an oriented molding by preparing a pre-molded material through melt molding of a biodegradable and bioabsorbable crystalline thermoplastic polymer material and then forcing the pre-molded material into a narrow space of a forming mold whose bottom part is substantially closed, while carrying out plastic deformation at a cold temperature and thereby effecting orientation by pressure deformation.

11. The method for producing a material for osteosynthesis according to claim 10, wherein the oriented molding is crystallized and has a crystalline form in which said crystals are oriented in parallel with a plurality of reference axes slanted toward an axis which becomes a mechanical core of said molding occurring along the pressure-charging direction in the forming mold and/or continued faces of said axis.

12. The method for producing a material for osteosynthesis according to claim 10, wherein the orientation by pressure deformation is effected by press-charging the pre-molded material of claim 10 into a forming mold which has a bottom part substantially closed and which has a smaller sectional area than the sectional area of said molding, while carrying out plastic deformation at a cold temperature and thereby effecting orientation by compression deformation.

13. The method for producing a material for osteosynthesis according to claim 10, wherein the orientation by pressure deformation is effected by forge-charging the pre-molded material of claim 10 into a narrow space of a forming mold having a space which is smaller, partially or as a whole, than the sectional area, thickness or width of said molding, or into a forming mold having a space which is smaller than the volume of the pre-molded material, while carrying out plastic deformation at a cold temperature and thereby effecting the orientation.

14. The method for producing a material for osteosynthesis according to any one of claims 10 to 13, wherein initial viscosity average molecular weight of said polymer material is from 200,000 to 600,000, and viscosity average molecular weight of the pre-molded material melt-formed thereafter is from 100,000 to 400,000.

15. The method for producing a material for osteosynthesis according to any one of claims 10 to 13, wherein the pre-molded material is press-charged into the cavity of a forming mold having a cross sectional area which is from $\frac{2}{3}$ to $\frac{1}{6}$ of the cross sectional area of the pre-molded material.

16. The method for producing a material for osteosynthesis according to any one of claims 10 to 13, wherein the forming mold comprises a container cylinder part having large sectional area where the pre-molded material is contained, a cavity having small sectional area where the pre-molded material is press-charged and a diameter-reducing part having a taper face which connects the above parts.

17. The method for producing a material for osteosynthesis according to any one of claims 10 to 13, wherein plastic deformation temperature of the pre-molded material is a temperature effective in performing crystallization, which is between the glass transition temperature and the melt temperature of said thermoplastic polymer material.

18. The method for producing a material for osteosynthesis according to any one of claims 10 to 13, wherein the oriented molding is made into a desired shape of the material for osteosynthesis by means of cutting work or the like.

19. A high strength implant material as a particle- and matrix polymer-reinforced composite material, which is a composite material comprising a pressure-oriented molding in which from 10 to 60% by weight of a bioceramics powder whose particle or aggregated mass of particles has a size of from 0.2 to 50 $\mu$m is dispersed substantially uniformly in matrix of a biodegradable and bioabsorbable crystalline thermoplastic polymer, wherein crystals of said matrix polymer are oriented by pressure and have a crystallinity of from 10 to 70%.

20. The high strength implant material according to claim 19, wherein the crystals of the said molding are oriented in parallel with a plurality of reference axes slanted toward an axis which becomes a mechanical core of said molding occurring along the pressure-charging direction in the forming mold and/or continued faces of said axis.

21. The high strength implant material according to claim 19 or 20, wherein the bioceramics powder is any one or a mixture of two or more of surface bioactive sintered hydroxylapatite, bioglass or crystallized glass for living body use, bioabsorbable un-sintered hydroxylapatite, dicalcium phosphate, tricalcium phosphate, tetracalcium phosphate and octacalcium phosphate.

22. The high strength implant material according to claim 19 or 20, wherein the biodegradable and bioabsorbable crystalline thermoplastic polymer is either a polylactic acid or a lactic acid-glycolic acid copolymer having an initial viscosity average molecular weight of from 100,000 to 600,000.

23. The high strength implant material according to claim 19 or 20, wherein the thermoplastic polymer is a polylactic acid and the bioceramics powder is an un-sintered hydroxylapatite.

24. The high strength implant material according to claim 19 or 20, wherein the said molding is an oriented molding obtained by pressure deformation orientation through a compression molding or a forging molding.

25. The high strength implant material according to claim 19 or 20, wherein the said oriented molding has a bending strength of from 150 to 320 MPa and a bending modulus of from 6 to 15 GPa.

26. The high strength implant material according to claim 19 or 20, wherein the said oriented molding is treated by means of cutting work or the like, and the bioceramics powder is exposed on the surface thereof.

27. A process for producing a high strength implant material by pressure deformation orientation, which comprises preparing in advance a mixture in which a biodegradable and bioabsorbable crystalline thermoplastic polymer and a bioceramics powder are dispersed in each other substantially uniformly, subsequently producing a pre-molded material by melt molding of said mixture, and then press-charging said pre-molded material at a cold temperature into the cavity of a closed forming mold to effect plastic deformation and formation of an oriented molding.

28. The process for producing a high strength implant material by pressure deformation orientation according to claim 27, wherein the said pressure orientation is effected by press charging at a cold temperature into the cavity of a closed forming mold having a smaller sectional area than that of the pre-molded material.

29. The process for producing a high strength implant material according to claim 27 or 28, wherein the pre-molded material is press-charged into the cavity of a closed forming mold in such a manner that crystallinity of the polymer of the pressure-oriented molding becomes from 10 to 70%.

30. The process for producing a high strength implant material according to claim 28 or 29, wherein the mixture of the said polymer and bioceramics powder is prepared by substantially uniformly mixing and dispersing the bioceramics powder in a solvent solution of the said polymer and subsequently precipitating the mixture with a non-solvent of said polymer.

31. The process for producing a high strength implant material according to claim 27 or 28, wherein the biodegradable and bioabsorbable crystalline thermoplastic polymer is a polylactic acid or a lactic acid-glycolic acid copolymer having an initial viscosity average molecular weight of from 150,000 to 700,000, and a viscosity average molecular weight of from 100,000 to 600,000 after its melt molding.

32. The process for producing a high strength implant material according to claim 27 or 28, wherein the pre-molded material is press-charged into the cavity of a forming mold having a cross sectional area which is from $\frac{2}{3}$ to $\frac{1}{5}$ of the cross sectional area of said pre-molded material.

33. The process for producing a high strength implant material according to claim 27 or 28, wherein plastic deformation temperature of the pre-molded material is a temperature effective in performing crystallization, which is between the glass transition temperature and the melt temperature of said polymer.

34. The process for producing a high strength implant material according to claim 27, wherein the orientation by pressure deformation is effected by compression orientation or forging orientation.

35. The process for producing a high strength implant material according to claim 27 or 28, wherein the said pressure-oriented molding is further processed by means of cutting work or the like.

\* \* \* \* \*